US010743842B2

(12) United States Patent
Tsushima

(10) Patent No.: US 10,743,842 B2
(45) Date of Patent: Aug. 18, 2020

(54) ULTRASOUND SIGNAL PROCESSOR, ULTRASOUND SIGNAL PROCESSING METHOD, AND ULTRASOUND DIAGNOSTIC DEVICE

(71) Applicant: Konica Minolta, Inc., Tokyo (JP)

(72) Inventor: Mineo Tsushima, Kyoto (JP)

(73) Assignee: KONICA MINOLTA, INC., Tokyo (JP)

(*) Notice: Subject to any disclaimer, the term of this patent is extended or adjusted under 35 U.S.C. 154(b) by 504 days.

(21) Appl. No.: 15/456,040

(22) Filed: Mar. 10, 2017

(65) Prior Publication Data
US 2017/0265845 A1 Sep. 21, 2017

(30) Foreign Application Priority Data
Mar. 18, 2016 (JP) ................... 2016-056225

(51) Int. Cl.
*A61B 8/00* (2006.01)
*G01S 7/52* (2006.01)
(Continued)

(52) U.S. Cl.
CPC ............. *A61B 8/5215* (2013.01); *A61B 8/06* (2013.01); *A61B 8/14* (2013.01); *A61B 8/4488* (2013.01);
(Continued)

(58) Field of Classification Search
None
See application file for complete search history.

(56) References Cited

U.S. PATENT DOCUMENTS

2002/0087218 A1* 7/2002 Amemiya ............ A61B 8/4411
700/19
2009/0326377 A1* 12/2009 Hirama ............... G01S 7/52046
600/447
(Continued)

FOREIGN PATENT DOCUMENTS

JP 2002224107 A 8/2002
JP 2005177338 A 7/2005
(Continued)

OTHER PUBLICATIONS

JPO, Notice of Reasons for Refusal for the corresponding Japanese patent application No. 2016-056225, dated Oct. 1, 2019, with English translation (11 pages).

*Primary Examiner* — Allen Porter
*Assistant Examiner* — Adreanne A. Arnold
(74) *Attorney, Agent, or Firm* — Lucas & Mercanti, LLP

(57) ABSTRACT

An ultrasound signal processor that selectively drives a plurality of transducer elements arrayed in an ultrasound probe and executes ultrasound transmission and reception to a subject to perform velocity analysis by a color flow mapping method includes: a transmitter configured to select a transmission transducer element array from the plurality of transducer elements and perform transmission from the transmission transducer element array; a receiver configured to generate a received signal sequence for a transducer element of a reception transducer element array; a phasing adder configured to generate an acoustic line signal; and a velocity calculator configured to generate a complex acoustic line signal and calculate an average velocity, wherein the phasing adder performs delay processing for changing a method for calculating a transmission time in which the ultrasound transmitted reaches each of the observation
(Continued)

points in at least one of the main target area and the sub-target area.

13 Claims, 19 Drawing Sheets

(51) Int. Cl.
    *G01S 15/88*     (2006.01)
    *A61B 8/08*     (2006.01)
    *G01S 15/89*     (2006.01)
    *A61B 8/06*     (2006.01)
    *A61B 8/14*     (2006.01)

(52) U.S. Cl.
    CPC ............ *A61B 8/488* (2013.01); *A61B 8/5207* (2013.01); *A61B 8/5223* (2013.01); *A61B 8/54* (2013.01); *G01S 7/52049* (2013.01); *G01S 15/8915* (2013.01); *G01S 15/8927* (2013.01); *G01S 15/8988* (2013.01); *G01S 15/8997* (2013.01); *G01S 7/52033* (2013.01)

(56) References Cited

U.S. PATENT DOCUMENTS

| | | | |
|---|---|---|---|
| 2015/0196273 A1* | 7/2015 | Yamamoto | A61B 8/5207 600/447 |
| 2015/0245818 A1* | 9/2015 | Zhai | A61B 8/488 600/453 |

FOREIGN PATENT DOCUMENTS

| | | |
|---|---|---|
| JP | 2011500261 A | 1/2011 |
| WO | 2014050885 A1 | 6/2015 |

* cited by examiner

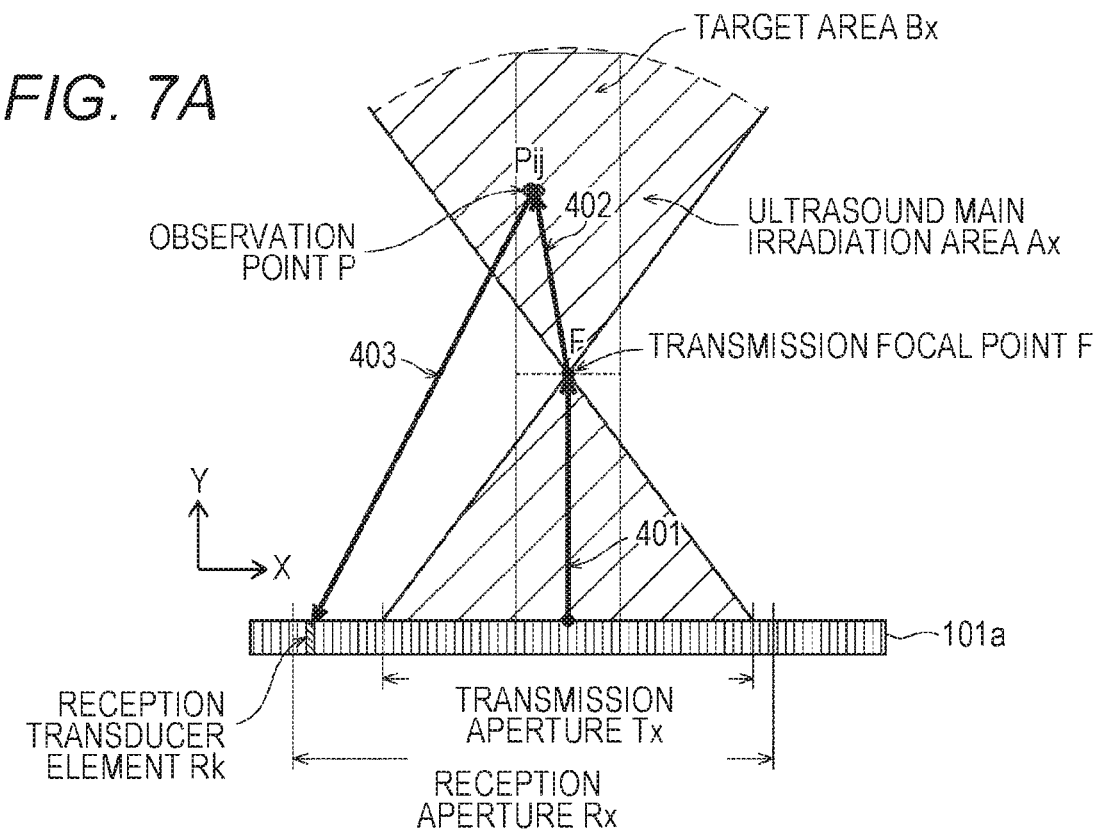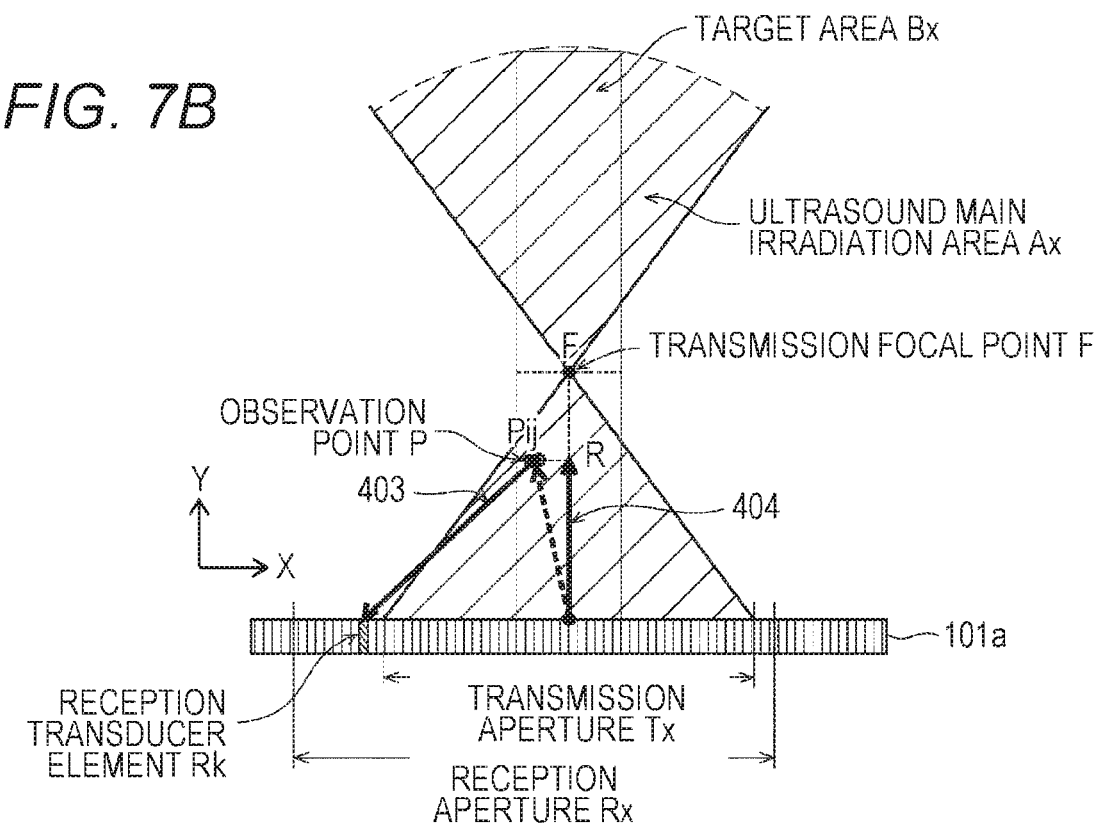

ULTRASOUND SIGNAL PROCESSOR, ULTRASOUND SIGNAL PROCESSING METHOD, AND ULTRASOUND DIAGNOSTIC DEVICE

The entire disclosure of Japanese Patent Application No. 2016-056225 filed on Mar. 18, 2016 including description, claims, drawings, and abstract are incorporated herein by reference in its entirety.

BACKGROUND OF THE INVENTION

Field of the Invention

The present invention relates to an ultrasound signal processor, an ultrasound signal processing method, and an ultrasound diagnostic device including the processor and the method, and in particular relates to a reception beam forming processing method in an ultrasound signal processor using a color flow mapping method, and color flow mapping calculation processing.

Description of the Related Art

An ultrasound diagnostic device transmits ultrasound to the inside of a subject with an ultrasound probe (hereinafter referred to as a "probe"), and receives reflected ultrasound (echo) caused by difference in acoustic impedance of subject tissue. Further, the ultrasound diagnostic device generates an image indicating a structure of internal tissue of the subject on the basis of an electric signal obtained from the received ultrasound, and displays the image on a monitor (hereinafter referred to as a "display"). The ultrasound diagnostic device has been widely used for morphological diagnosis of a living body since it is less invasive to the subject and a state of body tissue can be observed in real time with a tomographic image and the like.

In recent years, many ultrasound diagnostic devices are equipped with a color flow mapping (CFM) method. In the CFM method, a Doppler shift (frequency shift) is detected occurring in the echo caused by movement of body tissue such as a bloodstream, and velocity information as a two-dimensional image is superimposed and displayed on a two-dimensional tomographic image (B mode tomographic image). In order to detect the Doppler shift, it is necessary to transmit and receive the ultrasound repeatedly at the same position within the subject. Hereinafter, the number of times of transmitting and receiving the ultrasound to the same position is referred to as an "ensemble number," and an image generated with the CFM method is described as a "color Doppler image."

In the color Doppler image, image quality is improved as the ensemble number is increased; however, a problem has been known in which a frame rate is decreased since the number of times is increased of transmission and reception of ultrasound required. For that reason, a technique has been studied for improving quality of the color Doppler image regardless of the ensemble number, such as the technique disclosed in JP 2011-500261 A and JP 2005-177338 A, for example. In addition, a technique has been studied for improving the frame rate by not repeatedly performing transmission and reception of ultrasound to the same area by the ensemble number, such as the technique disclosed in JP 2002-224107 A, for example.

However, it is difficult to apply the techniques described in JP 2011-500261 A and JP 2005-177338 A when trying to improve the image quality by increasing the ensemble number. In addition, in the technique described in JP 2002-224107 A, there is a problem that it is not possible to keep the quality of the color Doppler image when trying to achieve further improvement of the frame rate.

SUMMARY OF THE INVENTION

The present invention has been made in view of the above problems, and it is an object to increase the ensemble number while keeping and without reducing the frame rate, and, further, to improve the quality of the color Doppler image.

To achieve the abovementioned object, according to an aspect, an ultrasound signal processor that selectively drives a plurality of transducer elements arrayed in an ultrasound probe and executes ultrasound transmission and reception to a subject to perform velocity analysis by a color flow mapping method, reflecting one aspect of the present invention comprises: a transmitter configured to select a transmission transducer element array from the plurality of transducer elements, and perform transmission from the transmission transducer element array such that ultrasound focuses within the subject, for a plurality of transmission events included in one of transmission event sets; a receiver configured to generate a received signal sequence for a transducer element of a reception transducer element array selected from the plurality of transducer elements, based on reflected ultrasound received by the transducer element, for each of the transmission events; a phasing adder configured to generate an acoustic line signal, for each of the transmission events, for a plurality of observation points included in a main target area including an area corresponding to an area in which the ultrasound focuses within the subject and a sub-target area adjacent to the main target area in an array direction, by performing phasing addition to the received signal sequence based on the reflected ultrasound obtained from each of the observation points; and a velocity calculator configured to generate a complex acoustic line signal by performing quadrature detection to the acoustic line signal for each of the transmission events, and calculate an average velocity, based on time change of a phase of the complex acoustic line signal for each of the observation points, wherein the phasing adder performs delay processing for changing a method for calculating a transmission time in which the ultrasound transmitted reaches each of the observation points, depending on a depth of each of the observation points, in at least one of the main target area and the sub-target area.

BRIEF DESCRIPTION OF THE DRAWINGS

The above and other objects, advantages and features of the present invention will become more fully understood from the detailed description given hereinbelow and the appended drawings which are given by way of illustration only, and thus are not intended as a definition of the limits of the present invention, and wherein:

FIGS. 7A and 7B are schematic views for describing a method for calculating a transmission time in a case in which the depth of an observation point is equal to or greater than the depth of a transmission focal point, and in a case in which the depth of the observation point is less than the depth of the transmission focal point, respectively;

DESCRIPTION OF THE PREFERRED EMBODIMENTS

Hereinafter, an embodiment of the present invention will be described with reference to the drawings. However, the scope of the invention is not limited to the illustrated examples.

<<Circumstances Leading to the Preferred Embodiments>>

The inventor has conducted various studies in order to achieve both an ensemble number and a frame rate in an ultrasound diagnostic device for generating a color Doppler image.

Figure 19A:
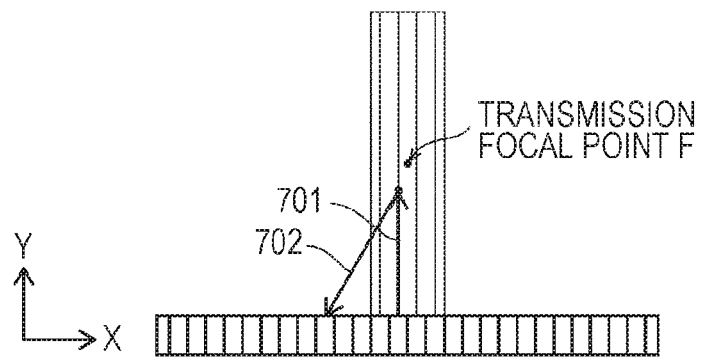
FIGS. 19A and 19B are schematic views illustrating reception beam forming and a target area in a conventional color flow mapping method.

Conventionally, transmission beam forming and reception beam forming as described below is performed in the ultrasound diagnostic device using a CFM method. FIG. 19A illustrates a schematic view. In the transmission beam forming, transmission beam forming is performed for causing a wave surface to focus so that an ultrasound beam is in focus on a certain point (hereinafter, referred to as a "transmission focal point") of a subject. In the reception beam forming, it is generally performed that an acoustic line signal for two to four elements is generated, from an area in which a transmission focus area is the center in the array direction. Multiple times of transmission and reception are performed of ultrasound in which the transmission focus area and a target area in which the acoustic line signal is generated are the same as each other, and the transmission and reception of ultrasound is performed by shifting the transmission focal point and the target area in which the acoustic line signal is generated, by the width in the array direction of the target area. That is, a position of the transmission focal point is constant in multiple acoustic line signals acquired from the same observation point. When it is assumed that the width in the array direction of the color Doppler image of one frame is a width of 192 elements, at least 48 transmission focal points have to be provided in order to generate an image of one frame. Therefore, when the ensemble number is ten, it is necessary to perform the transmission and reception of ultrasound at least 480 times that is the product of the number of transmission focal points and the ensemble number, in order to generate the color Doppler image of one frame, even when excluding acquisition of a B mode tomographic image. That is, the frame rate is inversely proportional to the ensemble number.

Therefore, in order to improve the frame rate, a technique has been studied for improving quality of the color Doppler image regardless of the ensemble number, as disclosed in JP 2011-500261 A and JP 2005-177338 A, for example. However, in these techniques, it is difficult to allow coexistence of benefit of image quality improvement due to an increase in the ensemble number and a benefit of image quality improvement due to the techniques, when it is desired to increase the ensemble number.

Figure 19B:
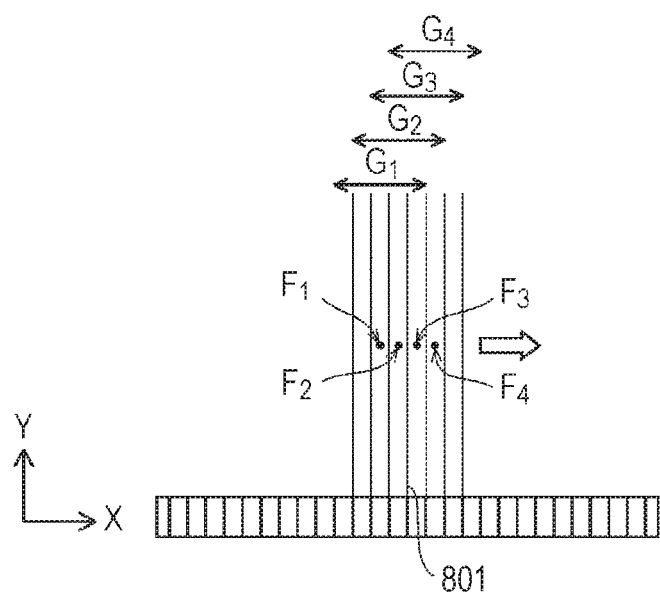

As a technique for achieving both the increase in the ensemble number and improvement of the frame rate, a technique has been studied for changing control methods between the transmission focus area and the target area in which the acoustic line signal is generated. The simplest technique is to enlarge an area in which an acoustic line is generated, for one transmission focal point. With this technique, it is possible to reduce the transmission focal points required for generating the color Doppler image of one frame, so that the frame rate can be improved. However, since a distance between the observation point and the transmission focal point differs for each acoustic line, there is a problem that a difference occurs in quality between an acoustic line signal close to the transmission focal point and an acoustic line signal far from the transmission focal point, and quality unevenness of the color Doppler image occurs in the array direction. Therefore, a technique of JP 2002-224107 A achieves reduction of the number of times of ultrasound transmission and reception while keeping the ensemble number, by making a smaller shift pitch between the transmission focus area and the target area in which the acoustic line signal is generated than the width in the array direction of a target distance. Specifically, acoustic line signals 801 are acquired in four types of transmission focal points and target areas, by using a target area G1 for a transmission focal point F1, a target area G2 for a transmission focal point F2, a target area G3 for a transmission focal point F3, and a target area G4 for a transmission focal point F4, as illustrated in a schematic view of FIG. 19B. However, also in this method, it has been found out that an effect is not sufficiently obtained of increasing the ensemble number due to quality degradation of the acoustic line signal far from the transmission focal point when enlarging the target area from about a size disclosed in JP 2002-224107 A.

Conventionally, in the reception beam forming, phasing addition is performed on the basis of the depth of the observation point as a reference. That is, a time in which the ultrasound passes through a shortest path 701 between an observation point P and a transducer element array is a transmission time in which the ultrasound transmitted from the transducer element array reaches the observation point P, as illustrated in FIG. 19A. A time in which the ultrasound passes through a path 702 between the observation point P and a reception transducer element is a reception time in which the ultrasound reflected from the observation point P reaches the reception transducer element. A sum of the transmission time and the reception time is a total propagation time, and the phasing addition is performed by performing delay processing to a received signal sequence generated by each reception transducer element using the total propagation time. This is for simplifying calculation since the amount of calculation is not small for generating the color Doppler image and a long time cannot be spent for signal processing of one ultrasound transmission and reception. In addition, when the width of the target area is as small as a width of about two to four elements, since an error is small between an actual time required for the ultrasound transmitted from the transducer element array to reach the observation point Panda calculated transmission time, quality of the color Doppler image does not degrade significantly even when the error is ignored. However, when the target area is enlarged, the error is increased between the actual time required for the ultrasound transmitted from the transducer element array to reach the observation point P and the calculated transmission time, as the position in the array direction is farther from the transmission focal point, that is, farther from the center in the array direction of the target area. As a result, because of quality degradation of the acoustic line signal due to the error, the effect is not sufficiently obtained of increasing the ensemble number.

Therefore, in consideration of the above problems, the inventor has conceived of an ultrasound signal processing method and an ultrasound diagnostic device using the method of embodiments, which suppress occurrence of the above error by improving a method for calculating a transmission time in the reception beam forming.

Hereinafter, detailed description will be made of the ultrasound image processing method and the ultrasound diagnostic device using the method of the embodiments, with reference to the drawings.

First Embodiment

<Entire Configuration>

Hereinafter, an ultrasound diagnostic device 100 of a first embodiment will be described with reference to the drawings.

Figure 1:
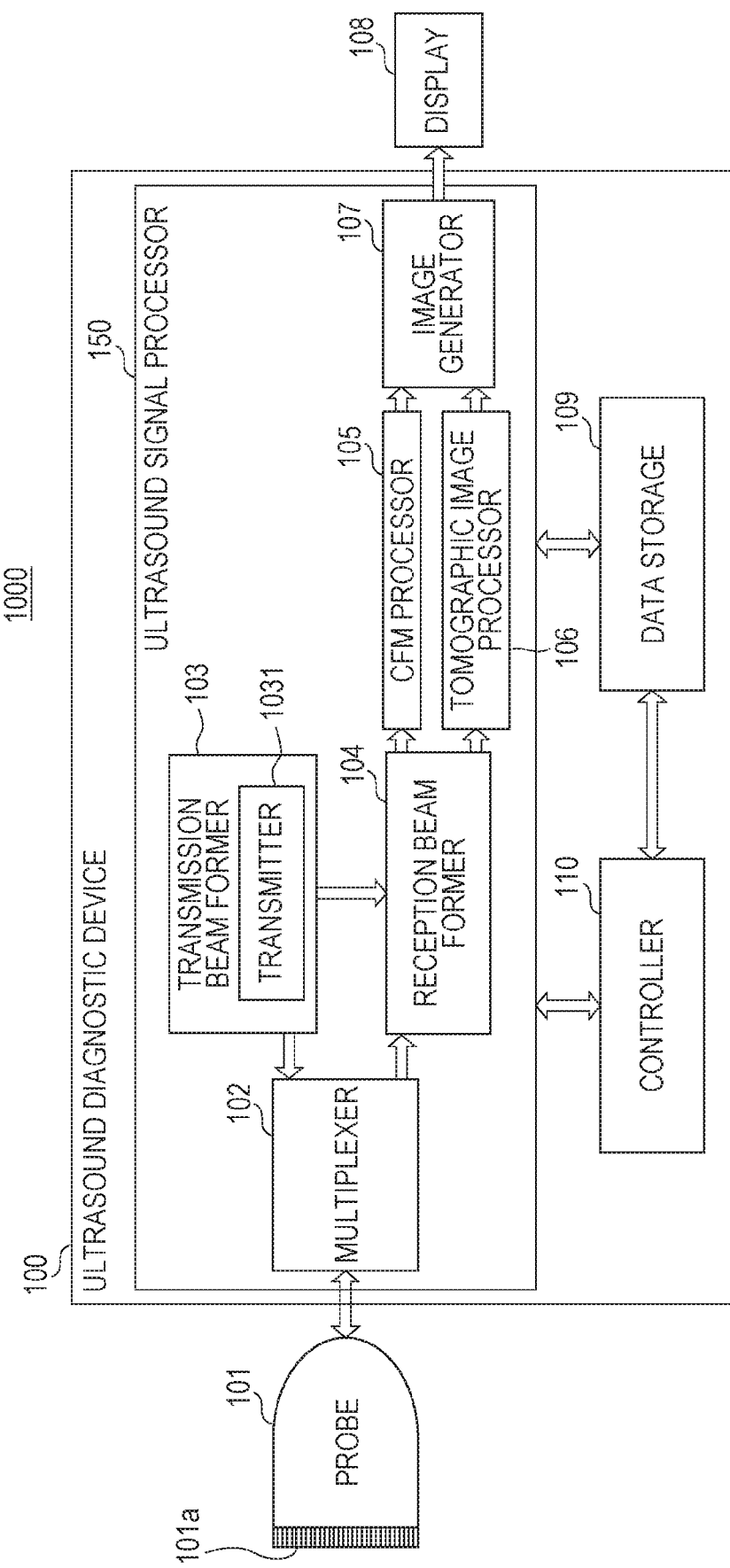
FIG. 1 is a functional block diagram of an ultrasound diagnostic system of a first embodiment.

FIG. 1 is a functional block diagram of an ultrasound diagnostic system 1000 of the first embodiment. As illustrated in FIG. 1, the ultrasound diagnostic system 1000 includes a probe 101 having multiple transducer elements 101a for transmitting ultrasound to a subject and receiving its reflected wave, an ultrasound diagnostic device 100 for causing the probe 101 to perform transmission and reception of ultrasound and generating a ultrasound image on the basis of an output signal from the probe 101, and a display 108 for displaying the ultrasound image on the screen. The probe 101 and the display 108 are each configured to be capable of connecting to the ultrasound diagnostic device 100. FIG. 1 illustrates a state in which the probe 101 and the display 108 are connected to the ultrasound diagnostic device 100. Incidentally, the probe 101 and the display 108 may be inside the ultrasound diagnostic device 100.

<Configuration of Ultrasound Diagnostic Device 100>

The ultrasound diagnostic device 100 includes: a multiplexer 102 for selecting transducer elements to be used for transmission or reception of the multiple transducer elements 101a of the probe 101, and securing input/output to the transducer elements selected; a transmission beam former 103 for controlling timing of high voltage application to each of the transducer elements 101a of the probe 101 in order to perform transmission of the ultrasound; and a reception beam former 104 for generating an acoustic line signal by performing amplification, A/D conversion, and reception beam forming to an electric signal obtained by the multiple transducer elements 101a, on the basis of the reflected ultrasound received by the probe 101. In addition, the ultrasound diagnostic device 100 includes: a CFM processor 105 for generating color flow information by performing frequency analysis to an output signal from the reception beam former 104, a tomographic image processor 106 for generating a frame acoustic line signal corresponding to a tomographic image (B mode image) on the basis of the output signal from the reception beam former 104; an image generator 107 for generating a color Doppler image by converting the frame acoustic line signal into a B mode tomographic image and superimposing the color flow information, and displaying the image on the display 108; a data storage 109 for storing the acoustic line signal output by the reception beam former 104, a frame CFM signal output by the CFM processor 105, and the frame acoustic line signal output by the tomographic image processor 106; and a controller 110 for controlling each component.

The multiplexer 102, the transmission beam former 103, the reception beam former 104, the CFM processor 105, the tomographic image processor 106, and the image generator 107 configure an ultrasound signal processor 150.

Each component configuring the ultrasound diagnostic device 100, for example, the multiplexer 102, the transmission beam former 103, the reception beam former 104, the CFM processor 105, the tomographic image processor 106, the image generator 107, and the controller 110, is implemented by a hardware circuit such as a field programmable gate array (FPGA), or an application specific integrated circuit (ASIC).

The data storage 109 is a computer readable recording medium, and, for example, a flexible disk, hard disk, MO, DVD, DVD-RAM, BD, semiconductor memory can be used. The data storage 109 may be a storage device externally connected to the ultrasound diagnostic device 100.

Incidentally, the ultrasound diagnostic device 100 of the present embodiment is not limited to the ultrasound diagnostic device having the configuration illustrated in FIG. 1. For example, the ultrasound diagnostic device 100 may have a configuration in which there is not the multiplexer 102, and the transmission beam former 103 and the reception beam former 104 are directly connected to each of the transducer elements 101a of the probe 101. In addition, the ultrasound diagnostic device 100 may have a configuration in which the transmission beam former 103, the reception beam former 104, or a part thereof is incorporated in the probe 101. This is not limited to the ultrasound diagnostic device 100 of the present embodiment, and the same applies to the ultrasound diagnostic device of other embodiments and modifications described later.

<Description of Components>

1. Transmission Beam Former 103

The transmission beam former 103 is connected to the probe 101 via the multiplexer 102, and controls timing of high voltage application to each of the multiple transducer elements included in a transmission aperture Tx including a transmission transducer element array corresponding to all or some of the multiple transducer elements 101a existing in the probe 101, in order to perform transmission of the ultrasound from the probe 101. The transmission beam former 103 is configured by a transmitter 1031.

The transmitter 1031 performs transmission processing for supplying a pulse transmission signal for causing each of the transducer elements included in the transmission aperture Tx of the multiple transducer elements 101a existing in the probe 101 to transmit an ultrasound beam, on the basis of transmission control signal from the controller 110. Specifically, the transmitter 1031 includes a clock generating circuit, a pulse generating circuit, and a delay circuit, for example. The clock generating circuit is a circuit for generating a clock signal for determining transmission timing of the ultrasound beam. The pulse generating circuit is a circuit for generating a pulse signal for driving each of the transducer elements. The delay circuit is a circuit for performing focusing of the ultrasound beam by delaying transmission of the ultrasound beam by a delay time, by setting the delay time of the transmission timing of the ultrasound beam for each of the transducer elements.

The transmitter 1031 performs ultrasound transmission from all transducer elements 101a existing in the probe 101 by repeating ultrasound transmission while shifting the transmission aperture Tx in the array direction by a predetermined shift pitch Mp for each series of ultrasound transmissions. Here, the shift pitch Mp is a product of the width in the array direction of the transducer elements and an integer equal to or greater than two, and is four times the width in the array direction of the transducer elements, as an example, in the present embodiment. The series of ultrasound transmissions is performed at least twice or more, and is performed ten times, as an example, in the present embodiment. That is, in the present embodiment, the transmission aperture Tx is shifted by the width of four elements for each ten ultrasound transmissions. Information indicating a position of each of the transducer elements included in the transmission aperture Tx is output to the data storage 109 via the controller 110. For example, when the total number of transducer elements 101a existing in the probe 101 is 192, for example 20-100 may be selected as the number of elements of the transducer element array configuring the transmission aperture Tx, and the transmitter 1031 may be configured to shift the transmission aperture Tx by the shift pitch Mp for each ultrasound transmission. Hereinafter, the series of ultrasound transmissions performed from the same transmission aperture Tx by the transmitter 1031 is collectively referred to as a "transmission event set," and each ultrasound transmission configuring the transmission event set is referred to as a "transmission event." Since an area that can be covered by one transmission is at most a few, it is necessary to perform the "transmission event" and the "transmission event set" so that an observation point is shifted and one surface can be covered in order to configure a color Doppler image of one frame. In the present embodiment, one transmission event set includes ten transmission events. That is, it is repeated that ultrasound transmission using the same transmission aperture Tx is performed ten times and then the transmission aperture Tx is shifted by the width of four elements, and ultrasound transmission using the same transmission aperture Tx is performed ten times and then the transmission aperture Tx is shifted by the width of four elements.

Figure 2:
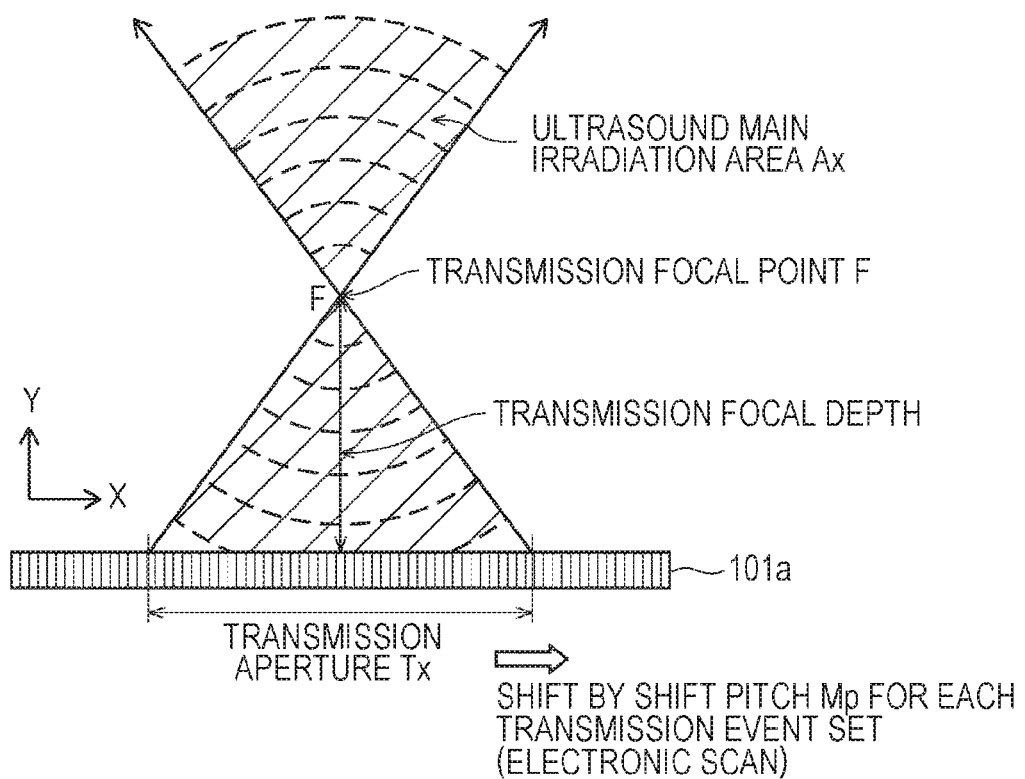
FIG. 2 is a schematic view illustrating a propagation path for an ultrasound transmission wave by a transmission beam former.

FIG. 2 is a schematic view illustrating a propagation path for an ultrasound transmission wave by the transmission beam former 103. An array (transmission transducer element array) is illustrated of the transducer elements 101a arranged in an array contributing to ultrasound transmission in a certain transmission event set, as the transmission aperture Tx. The array length of the transmission aperture Tx is referred to as a transmission aperture length.

In the transmission beam former 103, the transmission timing of each of the transducer elements is controlled so that the transducer elements positioned closer to the center of the transmission aperture Tx has a greater delay of the transmission timing. Thus, the ultrasound transmission wave transmitted from the transducer element array in the transmission aperture Tx has a state in which the wave surface is in focus (focuses) at a certain point, that is, a transmission focal point F (focal point), at a certain depth (focal depth) of the subject. The depth of the transmission focal point F (focal depth) (hereinafter, referred to as a "transmission focal depth") can be arbitrarily set. The wave surface focusing at the transmission focal point F diffuses again, and the ultrasound transmission wave propagates in an hourglass-shaped space that has the transmission aperture Tx as a base and is divided by two straight lines intersecting at the transmission focal point F. That is, the ultrasound radiated by the transmission aperture Tx gradually decreases the width in the space (the horizontal direction in the figure), and the width is minimized at the transmission focal point F, and again diffuses and propagates while increasing the width in accordance with progress to the deeper part (upper part in the figure) than the transmission focal point F. In other words, in the hourglass-shaped area, the width becomes greater as the depth is greater than the focal depth. The hourglass-shaped area is an ultrasound main irradiation area Ax. Incidentally, the transmission beam former 103 may be controlled so that the ultrasound focuses in an area in which there is the wave surface, that is, the transmission focus area, at the transmission focal depth.

Incidentally, the ultrasound main irradiation area Ax is an area in which phases of the ultrasound transmitted from the transducer elements of the transmission transducer element array are equal to each other, and the ultrasound transmission wave also propagates outside the ultrasound main irradiation area Ax. However, since the phases of the ultrasound transmitted from the transducer elements of the transmission transducer element array are not equal to each other outside the ultrasound main irradiation area Ax, the ultrasound transmission wave is degraded compared to that inside the ultrasound main irradiation area Ax, and in particular, the degradation is more remarkable as the ultrasound is farther from the ultrasound main irradiation area Ax. Conversely, in the vicinity separated from the ultrasound main irradiation area Ax by the width of about several transducer elements, the ultrasound transmission wave reaches in a degree by which a significant acoustic line can be generated.

2. Configuration of Reception Beam Former 104

Figure 3:
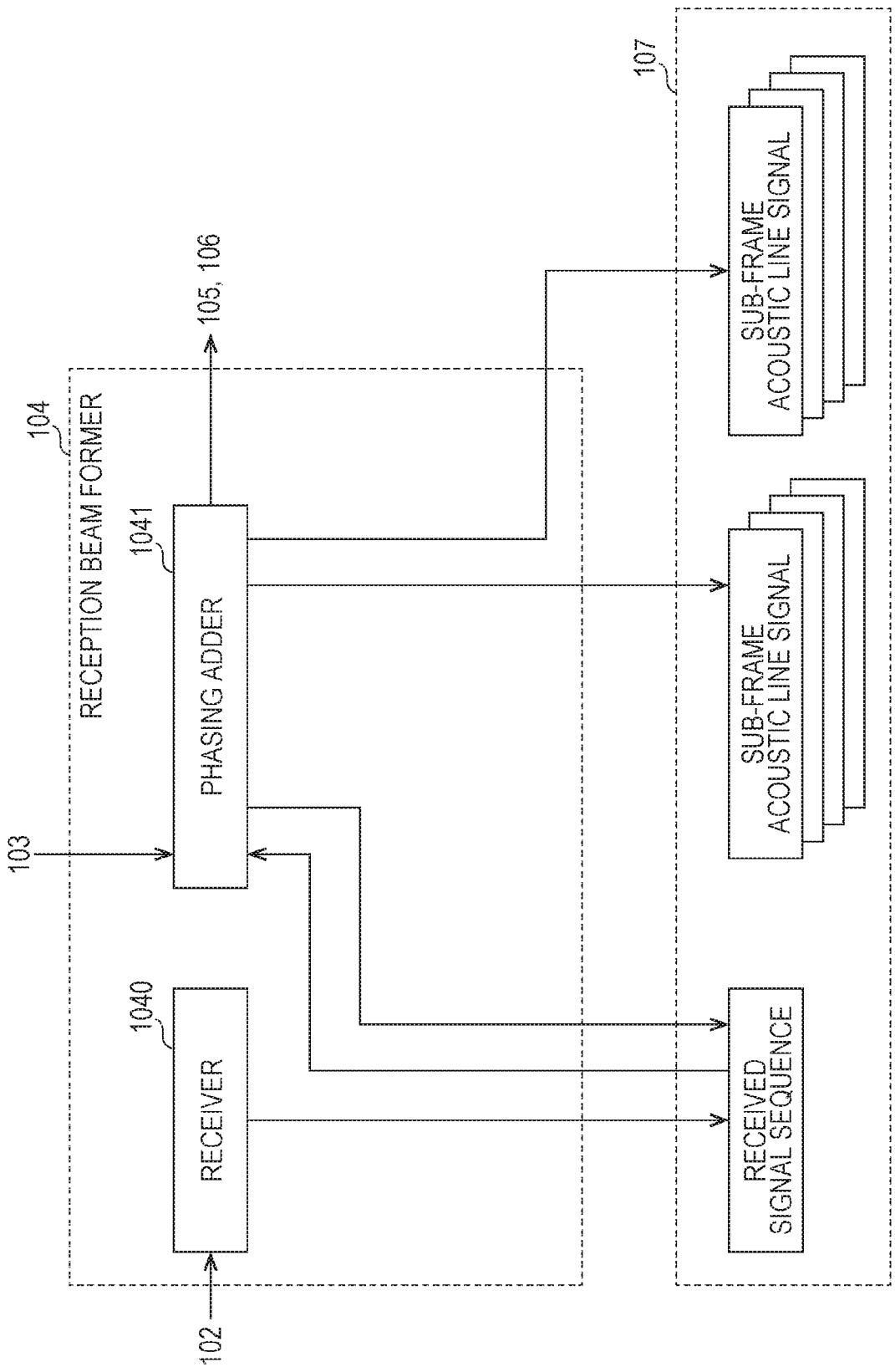
FIG. 3 is a functional block diagram illustrating a configuration of a reception beam former of the first embodiment.

The reception beam former 104 generates a sub-frame acoustic line signal from the electric signal obtained by the multiple transducer elements 101a, on the basis of the reflected ultrasound received by the probe 101. Incidentally, the "acoustic line signal" is a signal after phasing addition processing to a certain observation point is performed. The phasing addition processing will be described later. FIG. 3 is a functional block diagram illustrating a configuration of the reception beam former 104. As illustrated in FIG. 3, the reception beam former 104 includes a receiver 1040 and a phasing adder 1041.

Hereinafter, configurations will be described of the components configuring the reception beam former 104.

(1) Receiver 1040

The receiver 1040 is a circuit that is connected to the probe 101 via the multiplexer 102 and generates a received signal (RF signal) by performing amplification to the electric signal obtained from reception of the reflected ultrasound by the probe 101 in synchronization with the transmission event set and then performing A/D conversion. The received signal is generated in time series in order of the transmission event set and is output to the data storage 109, and the received signal is stored in the data storage 109.

Here, the received signal (RF signal) is a digital signal obtained by amplifying the electric signal converted from the reflected ultrasound received by each of the transducer elements and then performing A/D conversion, and forms a signal sequence continuing in a transmission direction (depth direction of the subject) of the ultrasound received by each of the transducer elements.

In the transmission event, as described above, the transmitter 1031 causes each of the multiple transducer elements included in the transmission aperture Tx of the multiple transducer elements 101a existing in the probe 101 to transmit the ultrasound beam. The receiver 1040 generates a received signal sequence for each of the transducer elements, on the basis of the reflected ultrasound obtained by each of the transducer elements corresponding to the multiple transducer elements 101a existing in the probe 101 in synchronization with the transmission event. Here, the transducer element receiving the reflected ultrasound is referred to as a "reception transducer element." The number of reception transducer elements is preferably greater than the number of transducer elements included in the transmission aperture Tx. The number of reception transducer elements may be the number of all transducer elements 101a existing in the probe 101.

The transmitter 1031 repeats ultrasound transmission while shifting the transmission aperture Tx in the array direction by a shift step Mp in synchronization with the transmission event set, and performs ultrasound transmission from the entire of the multiple transducer elements 101a existing in the probe 101. The receiver 1040 generates the received signal sequence for each reception transducer element in synchronization with the transmission event, and the received signal generated is stored in the data storage 109.

(2) Phasing Adder 1041

Figure 4:
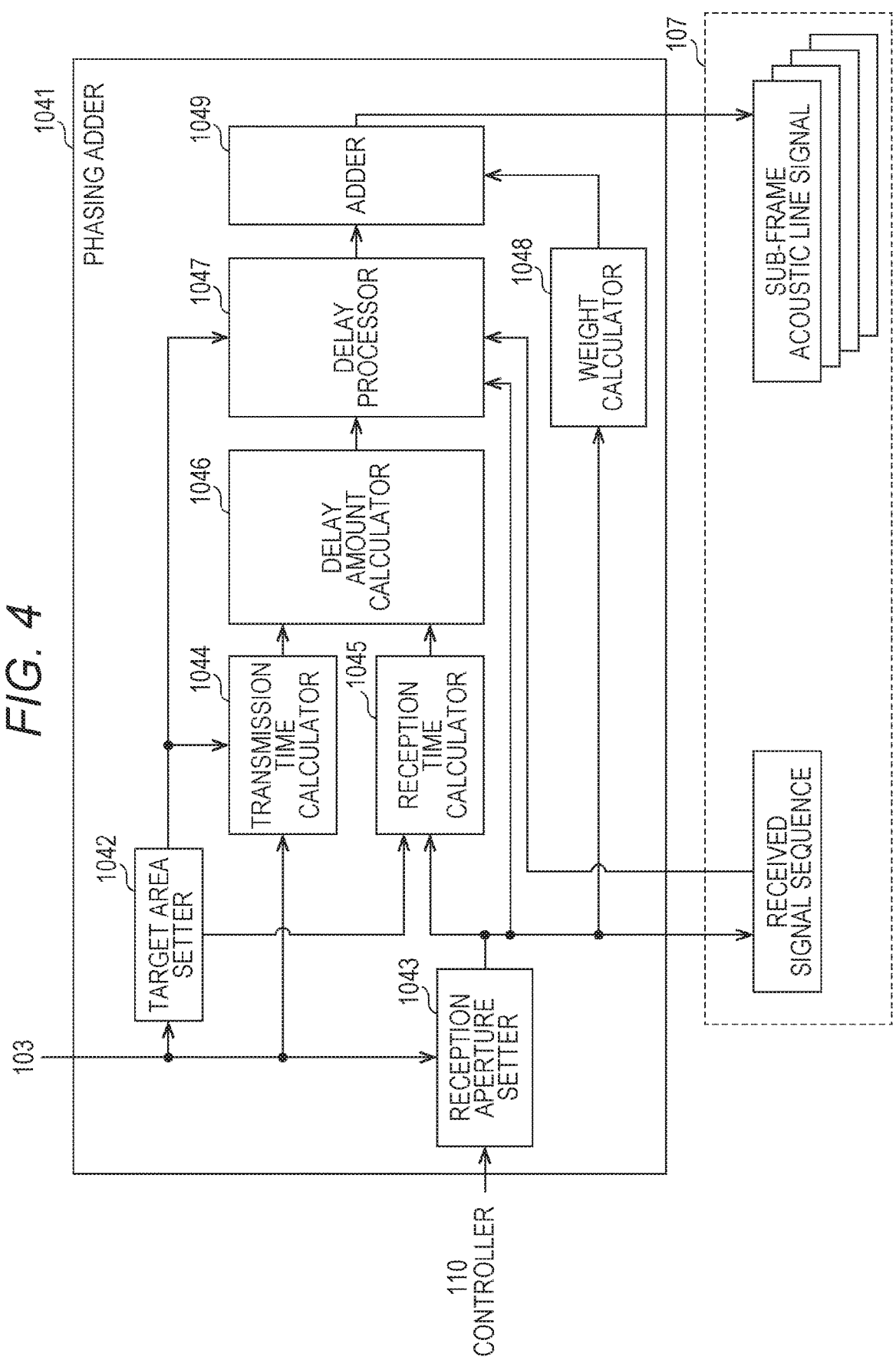
FIG. 4 is a functional block diagram illustrating a configuration of a phasing adder of the first embodiment.
Figure 5:
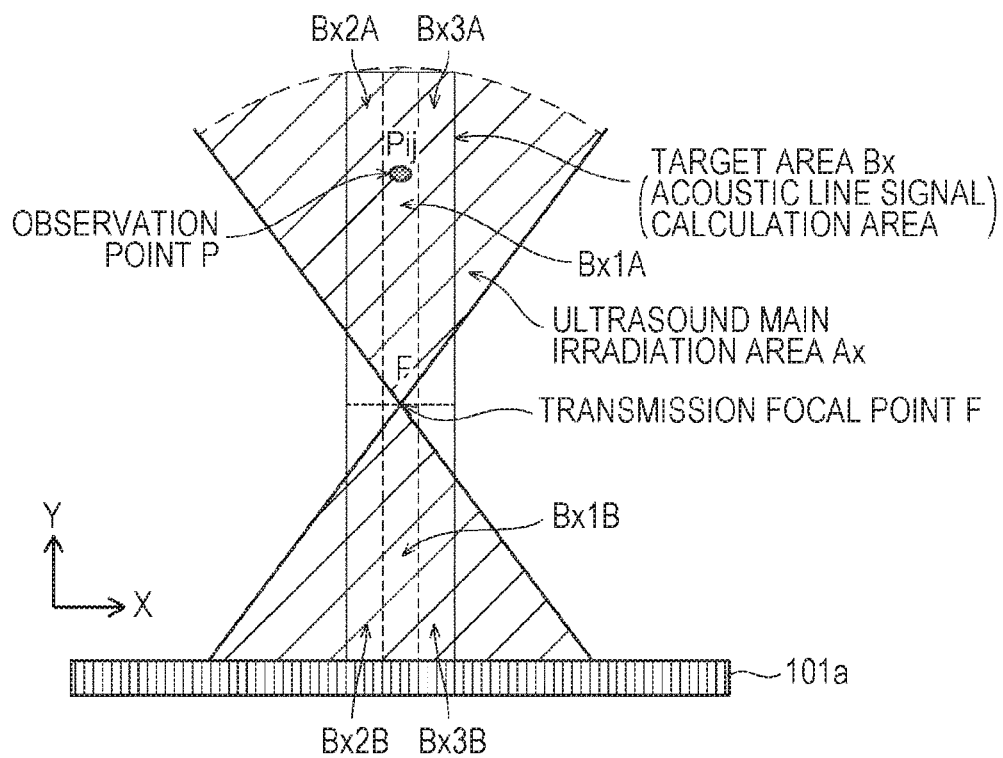
FIG. 5 is a schematic view illustrating a target area of the first embodiment.

The phasing adder 1041 is a circuit, and sets a target area Bx in which generation is performed of the sub-frame acoustic line signal within the subject, in synchronization with the transmission event set, as illustrated in FIG. 5. Next, for each of multiple observation points Pij existing in the target area Bx, phasing addition is performed to the received signal sequence received by each of reception transducer elements Rk from the observation points. Then, an acoustic line signal sequence at each observation point is calculated, whereby the sub-frame acoustic line signal is generated. FIG. 4 is a functional block diagram illustrating a configuration of the phasing adder 1041. As illustrated in FIG. 4, the phasing adder 1041 includes a target area setter 1042, a reception aperture setter 1043, a transmission time calculator 1044, a reception time calculator 1045, a delay amount calculator 1046, a delay processor 1047, a weight calculator 1048, and an adder 1049.

Hereinafter, configurations will be described of the components configuring the phasing adder 1041.

i) Target Area Setter 1042

The target area setter 1042 sets the target area Bx in which generation is performed of the sub-frame acoustic line signal within the subject, as illustrated in FIG. 5. The "target area" is an area on a signal in which generation is performed of the sub-frame acoustic line signal within the subject in synchronization with the transmission event set, and the acoustic line signal is generated for each of the observation points Pij within the target area Bx. The target area Bx is set for convenience of calculation in synchronization with one transmission event set, as a set of observation points in which generation is performed of the acoustic line signal.

Here, the "sub-frame acoustic line signal" is a set of the acoustic line signals for all observation points Pij existing in the target area Bx generated from one transmission event set. Incidentally, the "sub-frame" refers to a unit that forms a united signal corresponding to all observation points Pij existing in the target area Bx and is obtained in one transmission event set. A frame is obtained by synthesizing multiple sub-frames acquired at different times.

The target area setter 1042 sets the target area Bx on the basis of information indicating a position of the transmission aperture Tx acquired from the transmission beam former 103, in synchronization with the transmission event set.

FIG. 5 is a schematic view illustrating the target area Bx. As illustrated in FIG. 5, the range of the target area Bx is set to include the transmission focal point F and to have the width in the array direction of three times the transmission pitch Mp. In the present embodiment, the range has a rectangular shape that has the transmission focal point F as the center and has the width in the array direction of the width of twelve elements. Incidentally, when the transmission pitch Mp is the width of six elements, for example, the width in the array direction of the target area Bx is the width of 18 elements. Incidentally, the target area Bx is divided in the array direction into three areas of a main target area Bx1, and sub-target areas Bx2, Bx3. That is, the main target area Bx1 is an area that includes the transmission focal point F and has the width of four elements. In addition, the sub-target areas Bx2, Bx3 are adjacent to the main target area Bx1 in the array direction to sandwich the main target area Bx1A between them. Further, each of the main target area Bx1, the sub-target areas Bx2, Bx3 is divided into two areas on the basis of the depth of the transmission focal point F as a reference. That is, the main target area Bx1 is divided into an area Bx1A whose depth is equal to or greater than the depth of the transmission focal point F, and an area Bx1B whose depth is less than the depth of the transmission focal point F. Similarly, the sub-target area Bx2 is divided into an area Bx2A whose depth is equal to or greater than the depth of the transmission focal point F, and an area Bx2B whose depth is less than the depth of the transmission focal point F. Similarly, the sub-target area Bx3 is divided into an area Bx3A whose depth is equal to or greater than the transmission focal point F, and an area Bx3B whose depth is less than the depth of the transmission focal point F.

Incidentally, the observation point whose depth is equal to the transmission focal depth is included in any one of the main target area Bx1A, the sub-target areas Bx2A, Bx3A; however, it may be defined that each of the main target area Bx1A, the sub-target areas Bx2A, Bx3A is the area whose depth is greater than the depth of the transmission focal point F, and each of the main target area Bx1B, the sub-target areas Bx2B, Bx3B is the area whose depth is equal to or less than the depth of the transmission focal point F.

The target area Bx set is output to the transmission time calculator 1044, the reception time calculator 1045, and the delay processor 1047.

ii) Reception Aperture Setter 1043

The reception aperture setter 1043 is a circuit for setting the reception aperture Rx by selecting as the reception transducer element a transducer element array (reception transducer element array) that is a part of multiple transducer elements existing in the probe 101 and whose array center coincides with a transducer element spatially closest to the observation point P, on the basis of a control signal from the controller 110 and the information indicating the position of the transmission aperture Tx from the transmission beam former 103.

Figure 6:
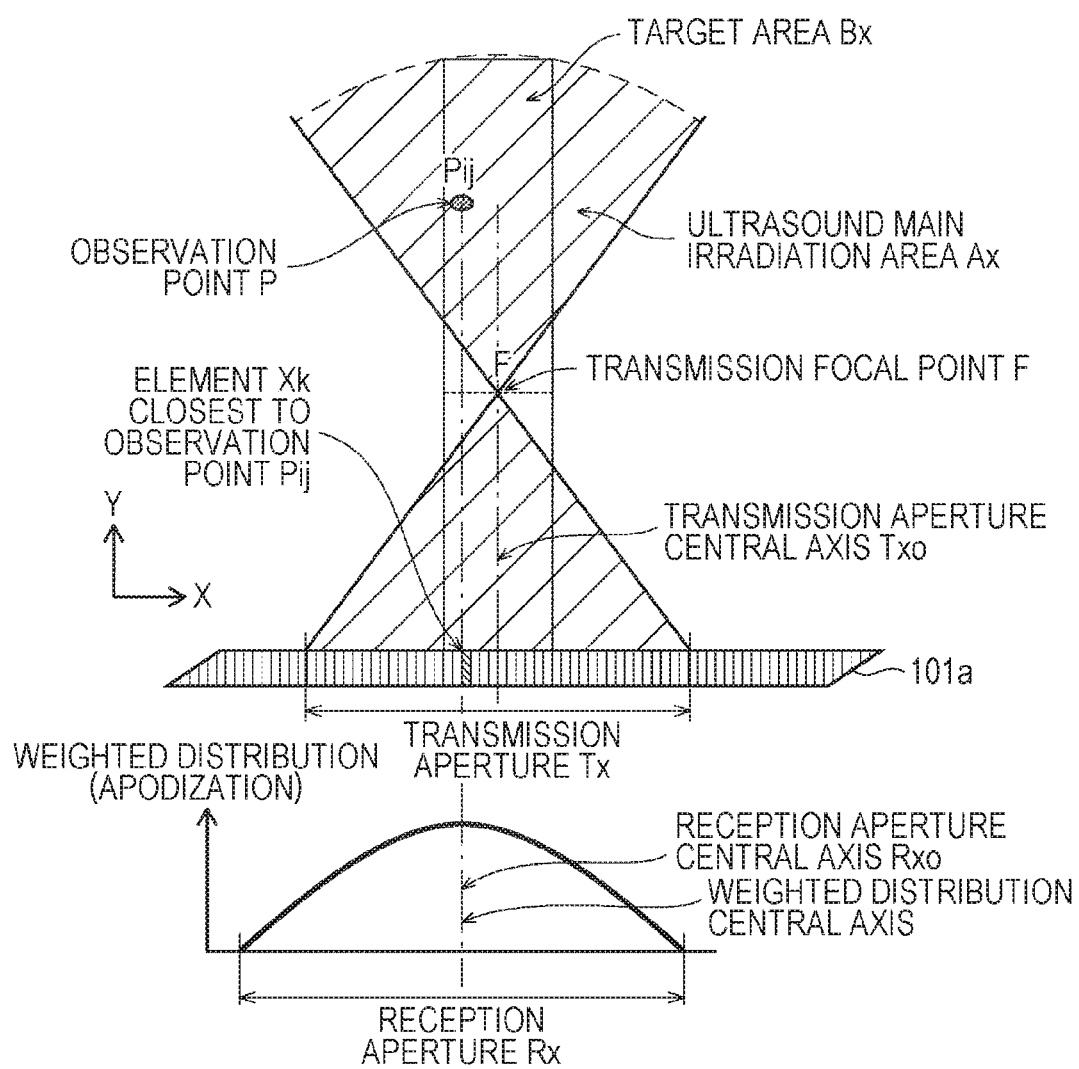
FIG. 6 is a schematic view illustrating a relationship between a reception aperture and a transmission aperture of the first embodiment.

The reception aperture setter 1043 selects a reception aperture Rx transducer element array so that the array center coincides with the transducer element spatially closest to the observation point P. FIG. 6 is a schematic view illustrating a relationship between the transmission aperture Tx and the reception aperture Rx set by the reception aperture setter 1043. As illustrated in FIG. 6, the reception aperture Rx transducer element array is selected so that the array center of the reception aperture Rx transducer element array coincides with a transducer element Xk spatially closest to the observation point Pij. For that reason, the position of the reception aperture Rx is determined by the position of the observation point Pij, and is not changed on the basis of the position of the transmission aperture Tx that fluctuates in synchronization with the transmission event set. That is, even in different transmission event sets, in processing for generating the acoustic line signal for the observation points Pij at the same position, the phasing addition is performed on the basis of the received signal acquired by a reception transducer element Ri in the same reception aperture Rx.

In order to receive reflected waves from the entire target area Bx, the number of transducer elements included in the reception aperture Rx is preferably set to be equal to or greater than the number of transducer elements included in the transmission aperture Tx in the corresponding transmission event set. The number of elements of the transducer element array configuring the reception aperture Rx may be 32, 64, 96, 128, 192, for example.

The setting of the reception aperture Rx is performed at least the number of times same as that of transmission event sets, correspondingly to the transmission event sets. The setting of the reception aperture Rx may be gradually performed in synchronization with the transmission event set, or the setting of the reception aperture Rx corresponding to each of the transmission event sets may be collectively performed the number of times of the transmission event sets, after all the transmission event sets are completed.

Information indicating the position of the reception aperture Rx selected is output to the data storage 109 via the controller 110.

The data storage 109 outputs the information indicating the position of the reception aperture Rx, and the received signal corresponding to the reception transducer element to the transmission time calculator 1044, the reception time calculator 1045, the delay processor 1047, and the weight calculator 1048.

iii) Transmission Time Calculator 1044

The transmission time calculator 1044 is a circuit for calculating a transmission time in which the ultrasound transmitted reaches the observation point P within the subject. The transmission time is calculated in which the ultrasound transmitted reaches an arbitrary observation point Pij within the subject, for the observation point Pij existing in the target area Bx, on the basis of the information indicating the position of the target area Bx acquired from the target area setter 1042 and the information indicating the position of each of the transducer elements included in the transmission aperture Tx acquired from the data storage 109, correspondingly to the transmission event set.

Here, the transmission time calculator 1044 changes a method for calculating the transmission time, in at least one combination of the main target areas Bx1A and Bx1B, the sub-target areas Bx2A and Bx2B, and the sub-target areas Bx3A and Bx3B. For example, the transmission time calculator 1044 changes the method for calculating the transmission time between the main target area Bx1A, the sub-target areas Bx2A, Bx3A, and the main target area Bx1B, the sub-target areas Bx2B, Bx3B.

FIGS. 7A and 7B are schematic views for describing a propagation path for the ultrasound that is radiated from the transmission aperture Tx, and is reflected at the observation point Pij existing in an arbitrary position within the target area Bx, and then reaches the reception transducer element Rk positioned in the reception aperture Rx. Here, FIG. 7A illustrates a case in which the observation point Pij exists in any one of the main target area Bx1A, the sub-target area Bx2A, and the sub-target area Bx3A, and FIG. 7B illustrates a case in which the observation point Pij exists in any one of the main target area Bx1B, the sub-target area Bx2B, and the sub-target area Bx3B.

First, the case will be described in which the observation point Pij exists in any one of the main target area Bx1A, the sub-target area Bx2A, and the sub-target area Bx3A. At this time, a calculation method is used based on the transmission focal point F as a reference. That is, calculation is performed assuming that the transmission wave radiated from the transmission aperture Tx reaches the transmission focal point F through a path 401, and reaches the observation point Pij through a path 402 from the transmission focal point F. Therefore, a transmission time $T_R$ is a sum of a time in which the transmission wave passes through the path 401 and a time in which the transmission wave passes through the path 402. As for a specific calculation method, for example, the transmission time is obtained by dividing the total path length obtained by adding the length of the path 401 and the length of the path 402 by a propagation velocity of the ultrasound within the subject.

The case will be described in which the observation point Pij exists in any one of the main target area Bx1B, the sub-target area Bx2B, and the sub-target area Bx3B, with reference to FIG. 7B. At this time, calculation is performed assuming that the transmission wave radiated from the transmission aperture Tx also reaches the observation point Pij at the time when the transmission wave reaches a reference point R having the same depth as the observation point Pij. Therefore, a transmission time $T_P$ is a time in which the transmission wave passes through a path 404 from the center of a transmission aperture Tx transducer element array to the reference point R. As for a specific calculation method, for example, the transmission time is obtained by dividing the length of the path 404 by the propagation velocity of the ultrasound within the subject.

The transmission time calculator 1044 calculates and outputs the transmission time in which the ultrasound transmitted reaches the observation point Pij within the subject, to the delay amount calculator 1046, for all observation points Pij within the target area Bx, for one transmission event set.

iv) Reception Time Calculator 1045

The reception time calculator 1045 is a circuit for calculating a reception time in which the reflected wave from the observation point P reaches each reception transducer element Rk included in the reception aperture Rx. The reception time is calculated in which the ultrasound transmitted is reflected at an arbitrary observation point Pij within the subject and reaches each reception transducer element Rk in the reception aperture Rx, for the observation point Pij existing in the target area Bx, on the basis of the information indicating the position of the target area Bx acquired from the target area setter 1042 and the information indicating the position of the reception transducer element Rk acquired from the data storage 109, correspondingly to the transmission event set.

The transmission wave reaching the observation point Pij generates the reflected wave when there is a change in acoustic impedance at the observation points Pij, and the reflected wave returns to each reception transducer element Rk in the reception aperture Rx in the probe 101. Since the positional information of each reception transducer element Rk in the reception aperture Rx is acquired from the data storage 109, the length of a path 403 from an arbitrary observation point Pij to each reception transducer element Rk can be geometrically calculated.

The reception time calculator 1045 calculates and outputs the reception time in which the ultrasound transmitted is reflected at the observation points Pij and reaches each reception transducer element Rk, to the delay amount calculator 1046, for all observation points Pij existing in the target area Bx, for one transmission event set.

v) Delay Amount Calculator 1046

The delay amount calculator 1046 is a circuit for calculating a total propagation time to each reception transducer element Rk in the reception aperture Rx from the transmission time and the reception time, and calculating a delay amount to be applied to the received signal sequence for each reception transducer element Rk, on the basis of the total propagation time. The delay amount calculator 1046 acquires a transmission time in which the ultrasound transmitted from the transmission time calculator 1044 reaches the observation point Pij, and a reception time in which the ultrasound is reflected at the observation point Pij and reaches each reception transducer element Rk. Then, the total propagation time is calculated in which the ultrasound transmitted reaches each reception transducer element Rk, and the delay amount is calculated for each reception transducer element Rk, from a difference of the total propagation time for each reception transducer element Rk. The delay amount calculator 1046 calculates and outputs the delay amount to be applied to the received signal sequence for each reception transducer element Rk, to the delay processor 1047, for all observation points Pij existing in the target area Bx.

vi) Delay Processor 1047

The delay processor 1047 is a circuit for identifying the received signal corresponding to the delay amount for each reception transducer element Rk as the received signal corresponding to each reception transducer element Rk based on the reflected ultrasound from the observation point Pij, from the received signal sequence for the acquired reception transducer element Rk in the reception aperture Rx, for each transmission event.

The delay processor 1047 acquires as inputs the information indicating the position of the reception transducer element Rk from the reception aperture setter 1043, the information indicating the position of the target area Bx acquired from the target area setter 1042, and the delay amount to be applied to the received signal sequence for each reception transducer element Rk from the delay amount calculator 1046, correspondingly to the transmission event set. Then, correspondingly to the transmission event, the delay processor 1047 acquires the received signal corresponding to the reception transducer element Rk as the input from the data storage 109, identifies the received signal corresponding to a time obtained by subtracting the delay amount for each reception transducer element Rk as the received signal based on the reflected wave from the observation points Pij in the transmission event, from the received signal sequence corresponding to each reception transducer element Rk, and outputs the received signal to the adder 1049.

vii) Weight Calculator 1048

The weight calculator 1048 is a circuit for calculating a weight sequence (reception apodization) for each reception transducer element Rk so that the weight is the maximum for the transducer element positioned at the center in the array direction of the reception aperture Rx.

As illustrated in FIG. 6, the weight sequence is a sequence of weighting factors to be applied to the received signals corresponding to each of the transducer elements in the reception aperture Rx. The weight sequence has a symmetric distribution around the transmission focal point F as the center. As the shape of the distribution of the weight sequence, a Hamming window, Hanning window, rectangular window, or the like can be used, and the shape of the distribution is not particularly limited. The weight sequence is set so that the weight is the maximum for the transducer element positioned at the center in the array direction of the reception aperture Rx, and a central axis of the weight distribution coincides with a reception aperture central axis Rxo. The weight calculator 1048 inputs the information indicating the position of the reception transducer element Rk output from the reception aperture setter 1043, and calculates and outputs the weight sequence for each reception transducer element Rk to the adder 1049.

viii) Adder 1049

The adder 1049 is a circuit for generating the acoustic line signal to which phasing addition is performed for the observation point Pij, by inputting and adding together the received signal that is identified correspondingly to each reception transducer element Rk and output from the delay processor 1047, for each transmission event. Alternatively, the adder 1049 may be configured to generate the acoustic line signal for the observation point Pij by further inputting the weight sequence for each reception transducer element Rk output from the weight calculator 1048, and multiplying the received signal identified correspondingly to each reception transducer element Rk by the weight for each reception transducer element Rk to add the signals together. Phasing is performed of the received signal detected by each reception transducer element Rk positioned in the reception aperture Rx and addition processing is performed in the adder 1049 in the delay processor 1047, whereby the signal S/N ratio can be increased by superimposing the received signals received by each reception transducer element Rk on the basis of the reflected wave from the observation point Pij, and the received signal from the observation point Pij can be extracted.

The acoustic line signal can be generated for all observation points Pij within the target area Bx from one transmission event and the processing accompanying the event. The adder 1049 repeats ultrasound transmission while shifting the transmission aperture Tx in the array direction by the shift pitch Mp in synchronization with the transmission event set, and performs ultrasound transmission from all transducer elements 101*a* existing in the probe 101, thereby generating multiple sub-frame acoustic line signals including the acoustic line signals for all observation points in one frame.

The sub-frame acoustic line signals are generated for all observation points Pij existing in the target area Bx in synchronization with the transmission event set, by the adder 1049. The sub-frame acoustic line signals generated are output and stored in the data storage 109.

3. Configuration of CFM Processor 105

Figure 8:
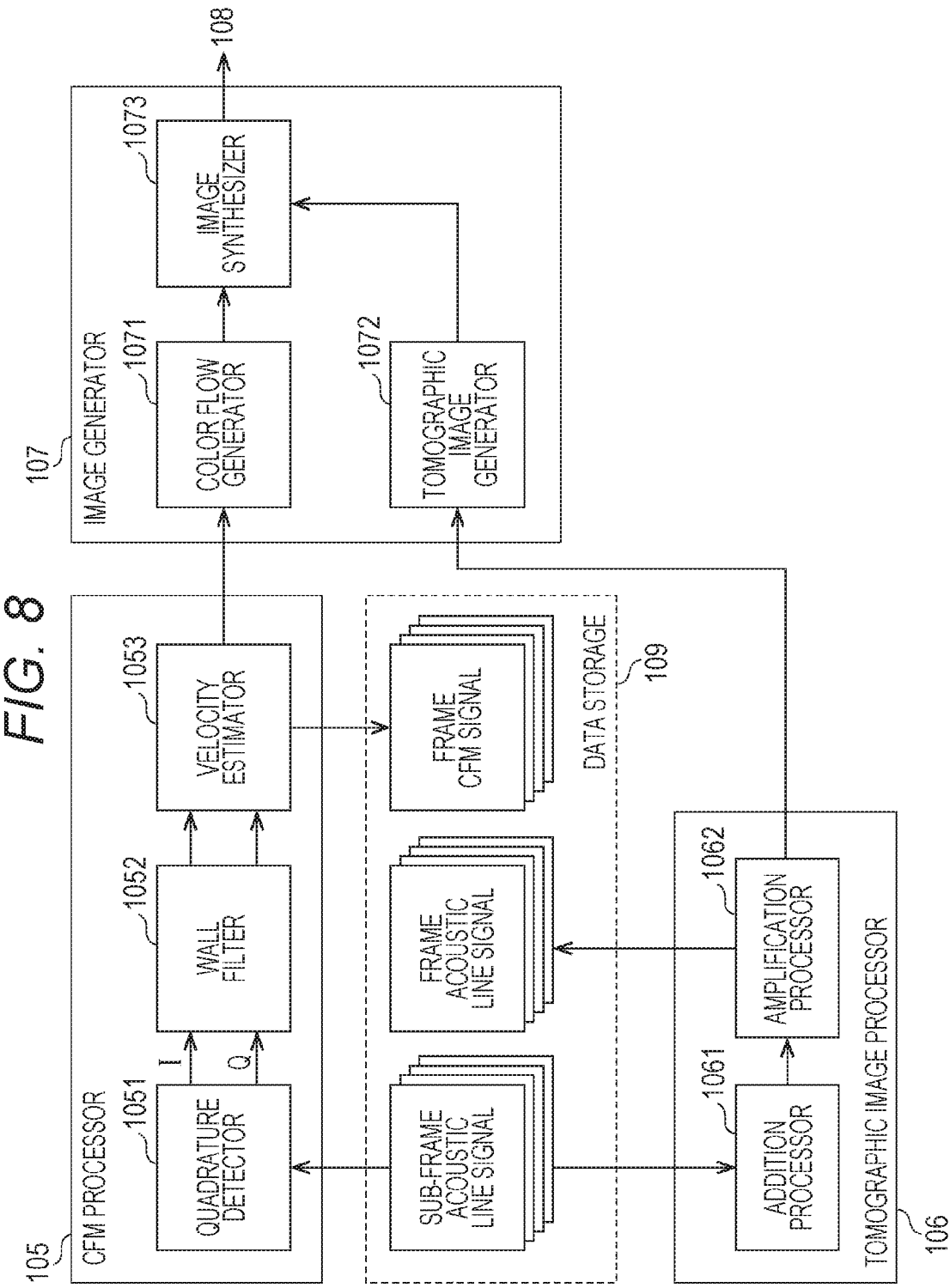
FIG. 8 is a functional block diagram illustrating configurations of a CFM processor, a tomographic image processor, and an image generator of the first embodiment.

The CFM processor 105 generates the frame CFM signal by performing frequency analysis on the basis of the multiple sub-frame acoustic line signals obtained in each of the multiple transmission event sets. Incidentally, the "CFM signal" is a signal indicating velocity information for a certain observation point. The velocity information will be described later. FIG. 8 is a functional block diagram illustrating configurations of the CFM processor 105, the tomographic image processor 106, and the image generator 107. As illustrated in FIG. 8, the CFM processor 105 includes a quadrature detector 1051, a filter 1052, and a velocity estimator 1053.

Hereinafter, configurations will be described of the components configuring the CFM processor 105.

(1) Quadrature Detector 1051

The quadrature detector 1051 is a circuit for generating a complex acoustic line signal indicating the phase of the received signal in each observation point by performing quadrature detection for each sub-frame acoustic line signal generated in synchronization with the transmission event. Specifically, the following processing is performed. First, a first reference signal having the same frequency as transmission ultrasound, and a second reference signal having the same frequency and amplitude as the first reference signal and a phase different by 90° are generated. Next, the acoustic line signal and the first reference signal are multiplied together, and the high frequency component having a frequency approximately twice the frequency of the first reference signal is removed by an LPF, to obtain a first component. Similarly, the acoustic line signal and the second reference signal are multiplied together, and the high frequency component having a frequency approximately twice the second reference signal is removed by the LPF, to obtain a second component. Finally, a complex acoustic line signal is generated with the first component as the real part (I component; In Phase) and the second component as the imaginary part (Q component; Quadrature Phase).

(2) Filter 1052

The filter 1052 is a filter circuit for removing clutter from the complex acoustic line signal. The clutter is a component not to be imaged of movement of tissue, and specifically is information indicating the movement of tissue such as a blood vessel wall, muscle, or organ. Since the clutter has greater power than a signal indicating a bloodstream, but the movement of tissue is slower than the bloodstream, the clutter has a lower frequency than the signal indicating the bloodstream. For that reason, it is possible to remove only the clutter selectively. A known so-called "wall filter," and a "moving target indicator (MTI) filter" can be applied to the filter 1052.

(3) Velocity Estimator 1053

Figure 9:
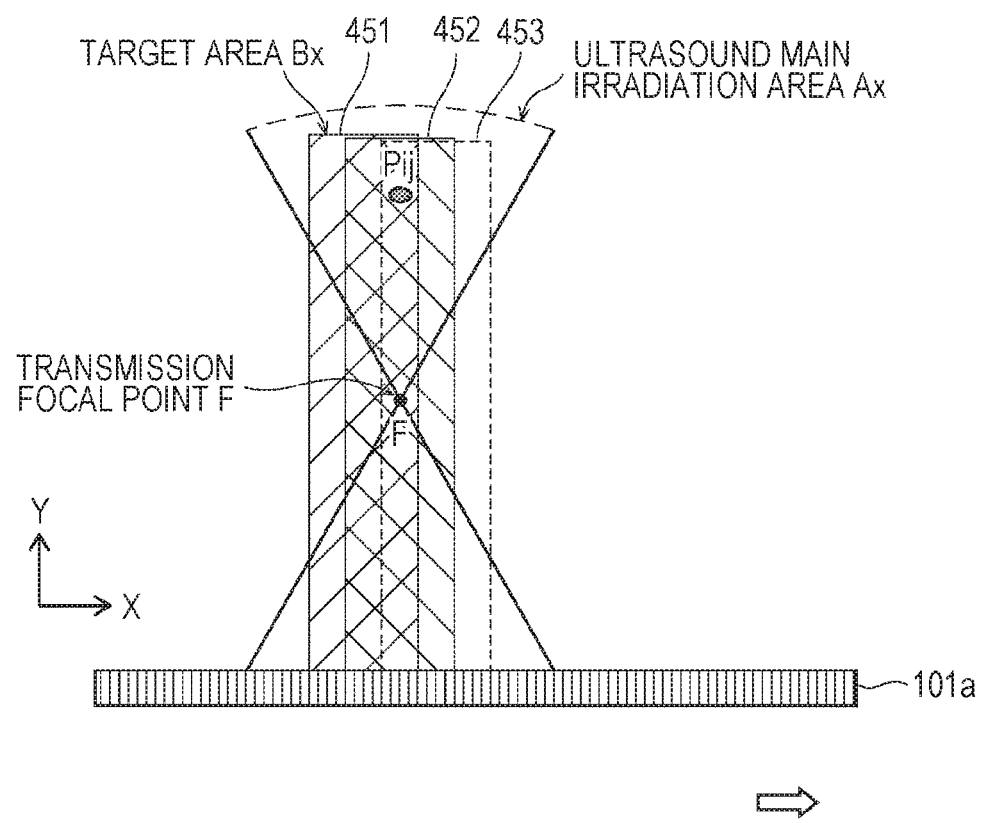
FIG. 9 is a schematic view illustrating operation of synthesis between transmission event sets in a velocity estimator of the first embodiment.

The velocity estimator 1053 is a circuit for estimating the movement, specifically the bloodstream, within the subject corresponding to each observation point from the complex acoustic line signal after being subjected to the filter processing. The velocity estimator 1053 estimates the phase from each complex acoustic line signal corresponding to the multiple transmission events of the multiple transmission event sets, and calculates a change rate of the phase, for each observation point. At this time, the complex acoustic line signal related to the same observation point is used without distinction, regardless of the transmission event in which the signal is acquired. FIG. 9 is a schematic view illustrating operation of synthesis between the transmission event sets in the velocity estimator 1053. In the observation point Pij illustrated in FIG. 9, ten acoustic line signals inside the sub-target area Bx3A are obtained, by ten transmission events, in the transmission event set having an area 451 as the target area Bx. Since the target area Bx is shifted by the width of four elements to be an area 452 in the next transmission event set, ten acoustic line signals inside the main target area Bx1A are obtained, for the observation point Pij. Since the target area Bx is shifted by the width of four elements to be an area 453 in a further next transmission event set, ten acoustic line signals inside the sub-target area Bx2A are obtained, for the observation point Pij. The velocity estimator 1053 uses the obtained 30 complex acoustic line signals as ensembles without distinction, and estimates the change rate of the phase, for the observation point P. Incidentally, the velocity estimator 1053 may estimate the change rate of the phase by performing correlation processing between the obtained 30 complex acoustic line signals.

The velocity estimator 1053 calculates a Doppler shift amount occurring each observation point from the change rate of the phase, and estimates an average velocity from the Doppler shift amount. The velocity estimator 1053 generates the frame CFM signal in which the average velocities are made to be a signal sequence continuing in the transmission direction (depth direction of the subject) of the ultrasound, and outputs the signal to the image generator 107 and the data storage 109. Incidentally, the velocity estimator 1053 may further calculate power and a variance value of velocity, on the basis of a power spectrum of the Doppler shift amount.

4. Configuration of Tomographic Image Processor 106

The tomographic image processor 106 synthesizes the sub-frame acoustic line signals obtained in each of the multiple transmission event sets, and generates the frame acoustic line signal that is a synthesized acoustic line signal of one frame. As illustrated in FIG. 8, the tomographic image processor 106 includes an addition processor 1061, and an amplification processor 1062.

Hereinafter, configurations will be described of the components configuring the tomographic image processor 106.

(1) Addition Processor 1061

The addition processor 1061 reads the multiple sub-frame acoustic line signals stored in the data storage 109, after generation is completed of a series of sub-frame acoustic line signals for synthesizing the frame acoustic line signal. Then, the addition processor 1061 generates a synthetic acoustic line signal for each observation point and synthesizes the frame acoustic line signal, by adding the multiple sub-frame acoustic line signals together using as an index the position of the observation point Pij in which the acoustic line signal included in each sub-frame acoustic line signal is acquired. For that reason, the acoustic line signals for the observation points of the same position included in the multiple sub-frame acoustic line signals are added together, and the synthetic acoustic line signal is generated.

In addition, since the value of the acoustic line signal in each sub-frame acoustic line signal is added to the observation point existing across multiple target areas of different positions, the synthetic acoustic line signal indicates a large value depending on the degree of overlap.

Incidentally, when performing addition using as an index the position of the observation point in which the acoustic line signal included in each sub-frame acoustic line signal is acquired, the addition processor 1061 may perform the addition while performing weighting using the position of the observation point as an index.

The frame acoustic line signal synthesized is output to the amplification processor 1062.

(2) Amplification Processor 1062

As described above, the value of the synthetic acoustic line signal changes depending on the amount of movement. In addition, the value also changes in the depth direction of the subject. To compensate for this, the amplification processor 1062 performs amplification processing in which each synthetic acoustic line signal is multiplied by an amplification factor determined in accordance with the number of times of performing addition, in synthesis of the synthetic acoustic line signal included in the frame acoustic line signal.

As for the amplification factor, since the maximum number of superimposition changes in the depth direction of the subject, a value is used that compensates for this change. Thus, the fluctuation factor of the synthetic acoustic line signal due to the change in the number of superimposition in the depth direction is eliminated, and the value of the synthetic acoustic line signal after the amplification processing is made uniform in the depth direction.

In addition, processing may be performed in which the synthetic acoustic line signal is multiplied by an amplification factor that changes in the transducer element array direction determined in accordance with the number of superimposition. In a case in which the number of superimposition changes in the transducer element array direction, the fluctuation factor is eliminated, and the value of the synthetic acoustic line signal after the amplification processing is made uniform in the transducer element array direction.

Incidentally, a signal obtained by performing amplification processing to the synthetic acoustic line signal for each observation point generated may be used as a frame acoustic line signal.

The amplification processor 1062 outputs the frame acoustic line signal to the image generator 107 and the data storage 109.

5. Configuration of Image Generator 107

The image generator 107 is a circuit for generating the color Doppler image by converting the frame acoustic line signal generated by the tomographic image processor 106 into the B mode tomographic image, and performing color tone conversion to the frame CFM signal generated by the CFM processor 105 to superimpose the signal on the image. As illustrated in FIG. 8, the image generator 107 includes a color flow generator 1071, a tomographic image generator 1072, and an image synthesizer 1073.

(1) Color Flow Generator 1071

The color flow generator 1071 is a circuit for performing color tone conversion for generating the color Doppler image from the frame CFM signal. Specifically, first, the coordinate system of the frame CFM signal is converted to an orthogonal coordinate system. Next, the average velocity of each observation point is converted into color information, and the color flow information is generated. At this time, for example, conversion is performed so that (1) the velocity in the direction toward the probe is red, and the velocity in the direction away from the probe is blue, and (2) the saturation is higher as the absolute value of the velocity is larger, and the saturation is lower as the absolute value is smaller. More specifically, the absolute value of the velocity is converted into the red luminance value for the velocity component going toward the probe, and the absolute value of the velocity is converted into the blue luminance value for the velocity component going away from the probe.

Incidentally, the color flow generator 1071 may further receive a signal indicating velocity variance from the CFM processor 105 and convert the value of the variance into the green luminance value. In this way, it is possible to indicate the position where turbulent flow occurs.

The color flow generator 1071 outputs the color flow information generated to the image synthesizer 1073.

(2) Tomographic Image Generator 1072

The tomographic image generator 1072 is a circuit for generating the B mode tomographic image from the frame acoustic line signal. Specifically, first, the coordinate system of the frame acoustic line signal is converted to an orthogonal coordinate system. Next, the value of the acoustic line signal of each observation point is converted into luminance, and the B mode tomographic image is generated. Specifically, the tomographic image generator 1072 performs conversion to the luminance by performing envelope detection to the value of acoustic line signal and performing logarithmic compression. The tomographic image generator 1072 outputs the B mode tomographic image generated to the image synthesizer 1073.

(2) Image Synthesizer 1073

The image synthesizer 1073 is a circuit for generating the color Doppler image by superimposing the color flow information generated by the color flow generator 1071 on the B mode tomographic image generated by the tomographic image generator 1072, and outputs the image to the display 108. Thus, the color Doppler image in which the direction and speed (absolute value of the velocity) of the bloodstream are added on the B mode tomographic image is displayed on the display 108.

<Operation>

Operation will be described of the ultrasound diagnostic device 100 configured as described above.

Figure 10:
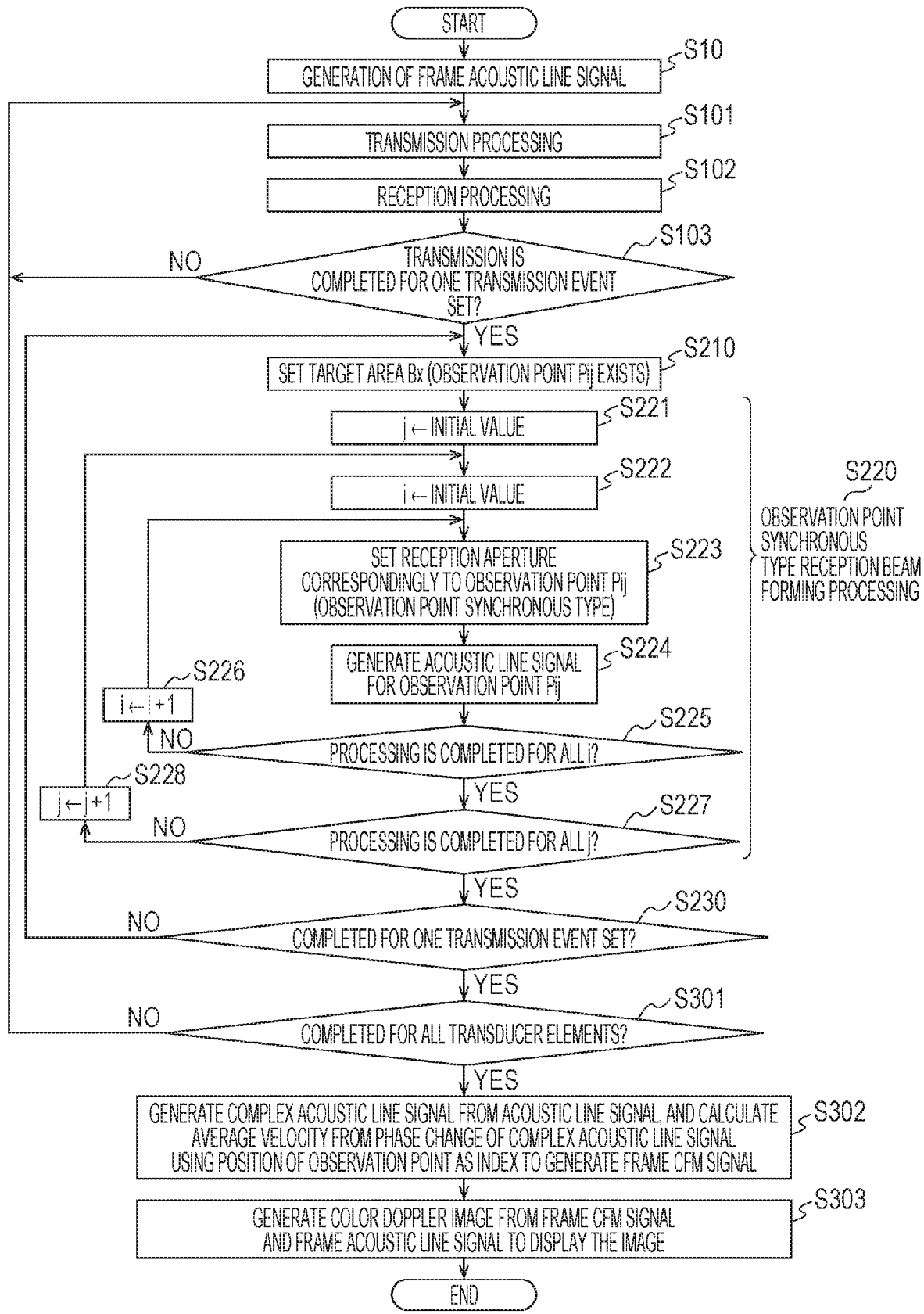
FIG. 10 is a flowchart illustrating operation of an ultrasound diagnostic device of the first embodiment.

FIG. 10 is a flowchart illustrating the operation of the ultrasound diagnostic device 100.

First, in step S10, the frame acoustic line signal is generated. Here, transmission processing (step S101) and reception processing (step S102) described later are each performed once for one target area (that is, a transmission event set including only one transmission event is performed), and the sub-frame acoustic line is generated by processing similar to step S220. Then, the tomographic image processor 106 synthesizes the multiple sub-frame acoustic line signals of one frame to generate the frame acoustic line signal. The frame acoustic line signal generated is output to the image generator 107 and the data storage 109.

Next, in step S101, the transmitter 1031 performs the transmission processing (transmission event) for supplying the transmission signal for causing each of the transducer elements included in the transmission aperture Tx of the multiple transducer elements 101a existing in the probe 101 to transmit the ultrasound beam.

Next, in step S102, the receiver 1040 generates the received signal on the basis of the electric signal obtained from reception of the reflected ultrasound by the probe 101 to output the signal to the data storage 109, and stores the received signal in the data storage 109. Then, it is determined that whether or not all transmission events included in one transmission event set are completed (step S103). When the transmission events are not completed, the operation returns to step S101, and the transmission events are performed by using the same transmission aperture. When the transmission events are completed, the operation proceeds to step S210.

Next, in step S210, the target area setter 1042 sets the target area Bx on the basis of the amount of movement and the information indicating the position of the transmission aperture Tx, in synchronization with the transmission event set. The target area Bx is set having a position in the array direction of the transmission focal point F as a central axis in the array direction.

Next, the operation proceeds to observation point synchronous type beam forming processing (step S220 (S221-S228)). In step S220, first, coordinates ij indicating the position of the observation point Pij is initialized to the minimum value within the target area Bx (steps S221, S222), and the reception aperture setter 1043 selects the reception aperture Rx transducer element array so that the array center coincides with the transducer element Xk spatially closest to the observation point Pij (step S223).

Next, the acoustic line signal is generated for the observation point Pij (step S224).

Figure 11:
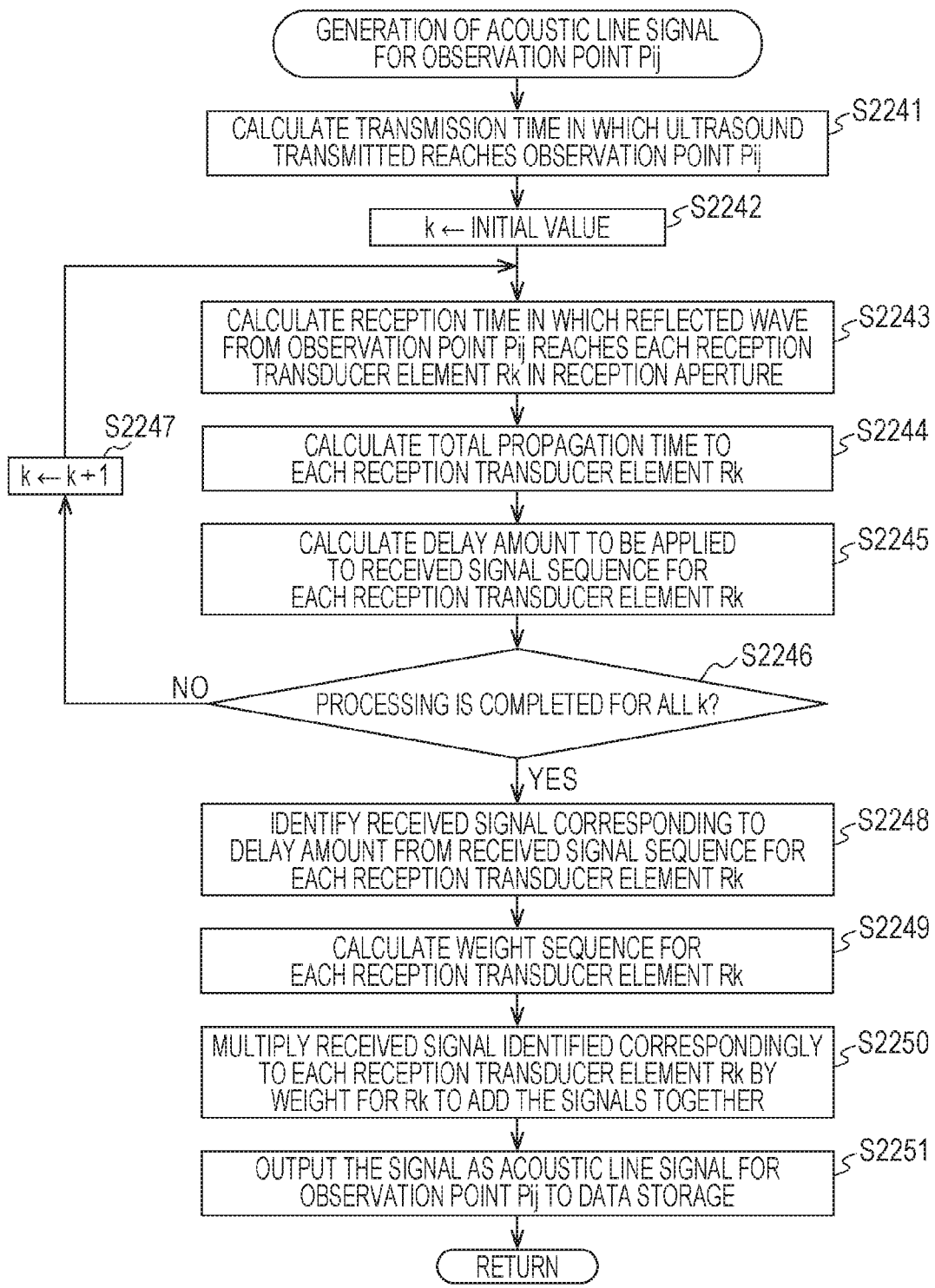
FIG. 11 is a flowchart illustrating generating operation of an acoustic line signal for the observation point in the reception beam former.

Here, operation will be described for generating the acoustic line signal for the observation point Pij in step S224. FIG. 11 is a flowchart illustrating operation for generating the acoustic line signal for the observation point Pij in the reception beam former 104.

First, in step S2241, the transmission time calculator 1044 calculates the transmission time in which the ultrasound transmitted reaches the observation point Pij within the subject, for an arbitrary observation point Pij existing in the target area Bx. The transmission time can be calculated by (1) dividing the length of the path (401+402) from the center of the transmission aperture Tx via the transmission focal point F to the observation point Pij, which is geometrically determined, by a sound speed cs of the ultrasound when the depth of the observation point Pij is equal to or greater than the focal depth, and (2) dividing the length of the path 404 from the center of the transmission aperture Tx to the reference point R having the same depth as the observation point Pij, which is geometrically determined, by the sound speed cs of the ultrasound when the depth of the observation point Pij is less than the focal depth.

Next, a coordinate k indicating the position of the reception transducer element Rk in the reception aperture Rx obtained from the reception aperture Rx is initialized to the minimum value in the reception aperture Rx (step S2242), and the reception time is calculated in which the ultrasound transmitted is reflected at the observation point Pij within the subject and reaches the reception transducer element Rk in the reception aperture Rx (step S2243). The reception time can be calculated by dividing the length of the path 403 from the observation point Pij to the reception transducer element Rk, which is geometrically determined, by the sound speed cs of the ultrasound. Further, a total propagation time is calculated in which the ultrasound transmitted from the transmission aperture Tx is reflected at the observation point Pij and reaches the reception transducer element Rk, from a total of the transmission time and the reception time (step S2244), and the delay amount is calculated for each reception transducer element Ri, from the difference of the total propagation time for each reception transducer element Rk in the reception aperture Rx (step S2245).

It is determined whether or not calculation of the delay amount is completed for all reception transducer elements Rk existing in the reception aperture Rx (step S2246), and when the calculation is not completed, an increment is performed to the coordinate k (step S2247), and the calculation is further performed of the delay amount for the reception transducer element Rk (step S2243), and when the calculation is completed, the operation proceeds to step S2248. At this stage, the delay amount has been calculated of arrival of the reflected wave from the observation point Pij for all reception transducer elements Rk existing in the reception aperture Rx.

In step S2248, the delay processor 1047 identifies the received signal corresponding to a time obtained by subtracting the delay amount for each reception transducer element Rk as the received signal based on the reflected wave from the observation point Pij in the transmission event, from the received signal sequence corresponding to the reception transducer element Rk in the reception aperture Rx, in each transmission event.

Next, the weight calculator 1048 calculates the weight sequence for each reception transducer element Rk so that the weight is the maximum for the transducer element positioned at the center in the array direction of the reception aperture Rx (step S2249). The adder 1049 generates the acoustic line signal for the observation point Pij by multiplying the received signal identified correspondingly to each reception transducer element Rk by the weight for each reception transducer element Rk and adding the signals together, for each transmission event (step S2250), and the acoustic line signal generated is output and stored in the data storage 109 (step S2251).

Returning to FIG. 10, description will be continued. The acoustic line signal is generated for all observation points Pij positioned in the coordinates ij within the target area Bx, by performing an increment to the coordinates ij and repeating the above steps S223, S224. It is determined whether or not generation of the acoustic line signal is completed for all observation points Pij existing in the target area Bx (steps S225, S227), and when the generation is not completed, an increment is performed to the coordinates ij (steps S226, S228), and the acoustic line signal is generated for the observation point Pij (step S224), and when the generation is completed, the operation proceeds to step S230. At this stage, the acoustic line signal for each transmission event has been generated, and output and stored in the data storage 109, for all observation points Pij existing in the target area Bx accompanied by one transmission event set.

Next, it is determined whether or not ultrasound transmission is completed from all transducer elements 101a existing in the probe 101 (step 230), and when the transmission is not completed, the operation returns to step S101, and the transmission event set is performed after the ultrasound transmission aperture Tx is shifted by a shift step Mp in the array direction. When the ultrasound transmission is completed, the operation proceeds to step S301. Thus, ten acoustic line signals acquired inside the main target area Bx1, ten acoustic line signals acquired inside the sub-target area Bx2, and ten acoustic line signals acquired inside the sub-target area Bx3 have been stored in the data storage 109, for one observation point.

Next, in step S301, the CFM processor 105 reads the multiple acoustic line signals stored in the data storage 109, and calculates the average velocity from a phase change of the complex acoustic line signal, using the position of the observation point Pij as an index. First, the quadrature detector 1051 performs quadrature detection to each acoustic line signal read and converts the signal to the complex acoustic line signal. The filter 1052 excludes or reduces the clutter from each complex acoustic line signal. Next, the velocity estimator 1053 estimates the change rate of the phase by performing correlation processing to the multiple complex acoustic line signals of the same observation point Pij. At this time, as described above, for the complex acoustic line signals of the same observation point Pij, distinction is not made for the transmission event set to which the acoustic line signal is related. Further, the velocity estimator 1053 calculates the Doppler shift amount from the change rate of the phase estimated, calculates the velocity from the Doppler shift amount, and calculates the average value of the velocity. Incidentally, the velocity estimator 1053 may calculate the average velocity on the basis of the average value of the Doppler shift amount, and may calculate the average Doppler shift amount from the average value of the change rate of the phase estimated. Finally, the velocity estimator 1053 generates the frame CFM signal by associating the average velocity calculated with the observation point, and outputs the signal to the image generator 107 and the data storage 109.

Next, in step S302, the image generator 107 generates and displays the color Doppler image. The color flow generator 1071 generates the color flow information from the frame CFM signal, and the tomographic image generator 1072 generates the B mode tomographic image from the frame acoustic line signal. Finally, the image synthesizer 1073 generates the color Doppler image by superimposing the color flow information on the B mode tomographic image, and outputs the image to the display 108.

<Summary>

As described above, with the ultrasound diagnostic device 100 of the present embodiment, the color flow mapping method is performed on the basis of the multiple acoustic line signals for the observation point P that has the same position and is generated by the different transmission event sets. Thus, in comparison with a case in which ultrasound is repeatedly transmitted and received as many times as the ensemble number to the same area, it is possible to reduce the number of times of transmission and reception of ultrasound while keeping the ensemble number, and to improve the frame rate while keeping quality of the color Doppler image.

In addition, in the ultrasound diagnostic device 100, the reception beam forming method is made to differ on the basis of the depth of the transmission focal point F as a reference. Thus, the beam forming suitable for a deep area and the beam forming suitable for a shallow area can be used properly, so that quality of the acoustic line signal can also be improved for the observation point P far from the transmission focal point F. Therefore, the quality of the acoustic line signal does not fluctuate greatly depending on whether the observation point P is far from or close to the transmission focal point F, and degradation in quality of the color Doppler image can be suppressed even when the target area is enlarged. Therefore, the quality degradation of the color Doppler image can be suppressed even when the target area is expanded for improving the frame rate.

First Modification

In the ultrasound diagnostic device 100 of the first embodiment, the phasing adder 1041 is configured to switch two types of methods for calculating the transmission time depending on whether the depth of the observation point P is equal to or greater than, or less than the depth of the transmission focal point F. However, the method for calculating the transmission time is not limited to the two types described in the first embodiment, and also, the reference of the switching is not limited to whether the depth of the observation point P is equal to or greater than, or less than the depth of the transmission focal point F and can be changed if appropriate.

<Method for Calculating Transmission Time>

Hereinafter, a method will be described for calculating the transmission time that can be used other than the method described in the first embodiment.

Figure 12A:
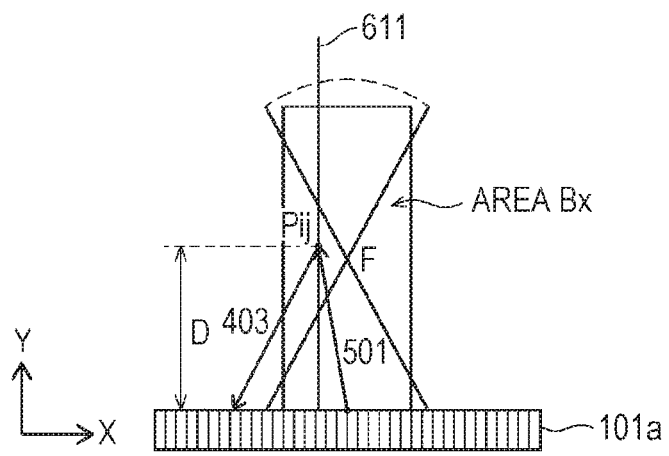
FIGS. 12A and 12B are both schematic views for describing another method for calculating a transmission time in a case in which the depth of the observation point is equal to or greater than the depth of the transmission focal point.
Figure 12B:
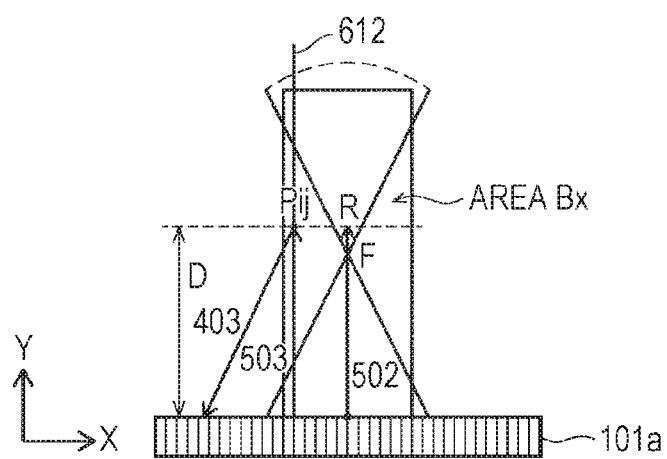

FIGS. 12A and 12B are schematic views each describing a method for calculating the transmission time that can be used in a case in which the depth of the observation point P is equal to or greater than the depth of the transmission focal point F. The method illustrated in FIG. 12A is a method in which a transmission time $T_D$ is a time in which the ultrasound passes through a path 501 from the center of the transmission aperture Tx to the observation point Pij, for the observation point Pij on a straight line 611 orthogonal to the transducer element array. That is, the transmission time $T_E$ is a value obtained by dividing the length of the path 501 by the sound speed cs of the ultrasound. The method illustrated in FIG. 12B is a method in which the transmission time $T_P$ is a time in which the ultrasound passes through a shortest path 502 from the transmission aperture Tx to the reference point R having the same depth as the observation points Pij, for the observation point Pij on a straight line 612 orthogonal to the transducer element array. That is, the transmission time $T_P$ is a value obtained by dividing the length of the path 502 by the sound speed cs of the ultrasound. Incidentally, not limited to the methods for calculating the transmission time described above, a transmission time $T_N$ may be calculated on the basis of a path from an arbitrary point on the transmission aperture Tx to an arbitrary point having the same depth as the observation point Pij.

Figure 13A:
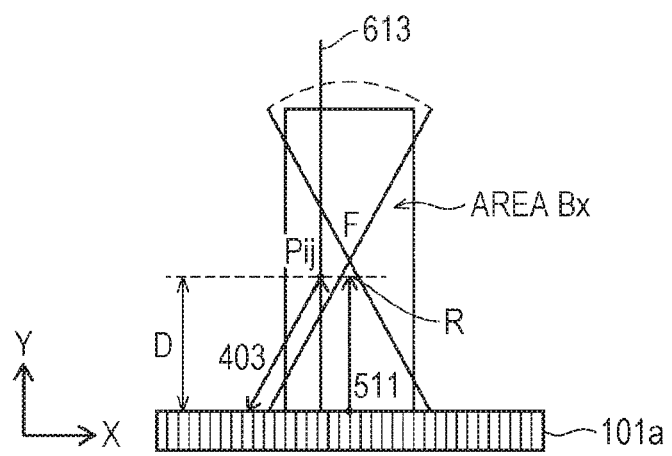
FIGS. 13A and 13B are both schematic views for describing another method for calculating a transmission time in a case in which the depth of the observation point is less than the depth of the transmission focal point.
Figure 13B:
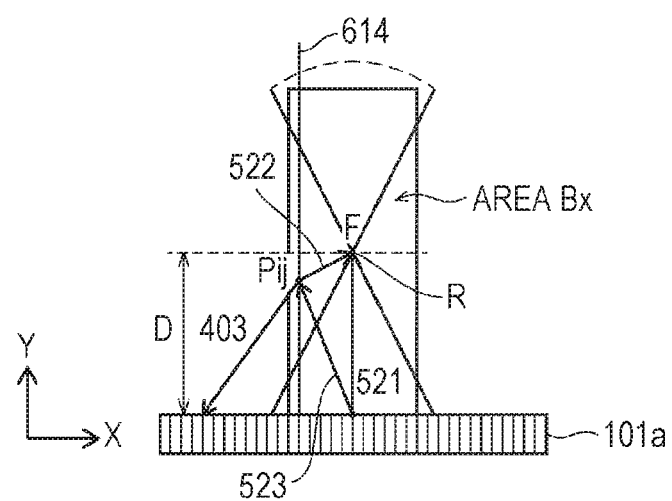

FIGS. 13A and 13B are schematic view each describing a method for calculating the transmission time that can be used in a case in which the depth of the observation point P is less than the depth of the transmission focal point F. The method illustrated in FIG. 13A is a method in which the transmission time $T_D$ is a time in which the ultrasound passes through a shortest path 511 from the transmission aperture Tx to the reference point R having the same depth as the observation points Pij, for the observation point Pij on a straight line 613 orthogonal to the transducer element array. That is, the transmission time $T_D$ is a value obtained by dividing the length of the path 511 by the sound speed cs of the ultrasound. Incidentally, not limited to the methods for calculating the transmission time described above, a transmission time $T_N$ may be calculated on the basis of a path from an arbitrary point on the transmission aperture Tx to an arbitrary point having the same depth as the observation point Pij. The method illustrated in FIG. 13B is a calculation method on the basis of the transmission focal point F as a reference. That is, a method for calculating a transmission time $T_R$ by assuming that the ultrasound reaching the transmission focal point F directly from the transmission aperture Tx and the ultrasound reaching the transmission focal point F via the observation point Pij reach the transmission focal point F at the same time, for the observation point Pij on a straight line 614 orthogonal to the transducer element array. That is, the distance of the path 523 is calculated by assuming that the distance of a path 521 and a total distance of a path 523 and a path 522 are the same as each other, in which the path 521 is from the center of the transmission aperture Tx to the transmission focal point F, the path 523 is from the center of the transmission aperture Tx to the observation point Pij, and the path 522 is from the observation point Pij to the transmission focal point F. Therefore, a difference obtained by subtracting the length of the path 522 from the length of the path 521 is divided by the sound speed cs of the ultrasound, whereby the value is obtained as the transmission time $T_R$.

Further, the following method may be used for calculating a transmission time. That is a method in which various calculation methods described above are combined. For example, the following calculation method $T_M$ can be used.

Figure 14A:
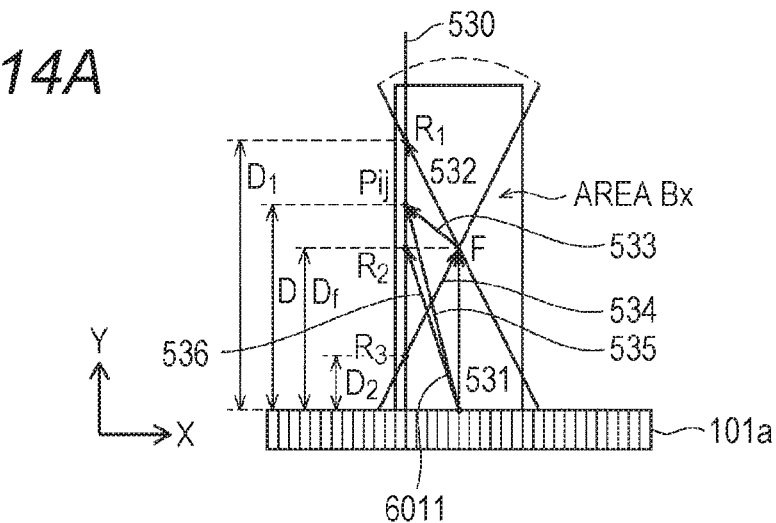
FIGS. 14A to 14C are all schematic views for describing another method for calculating a transmission time.
Figure 14B:
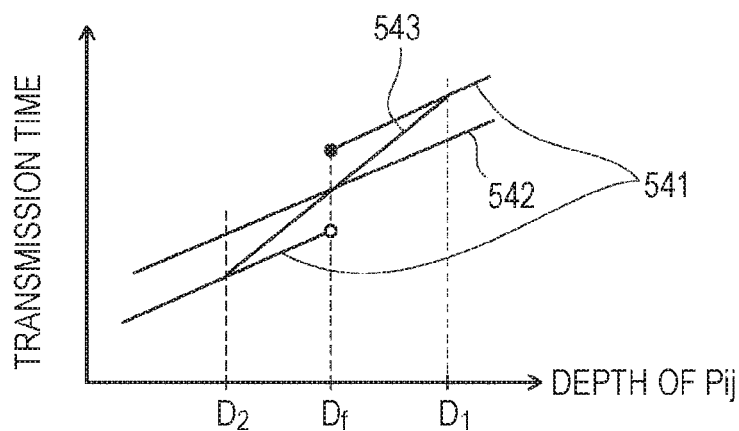
Figure 14C:
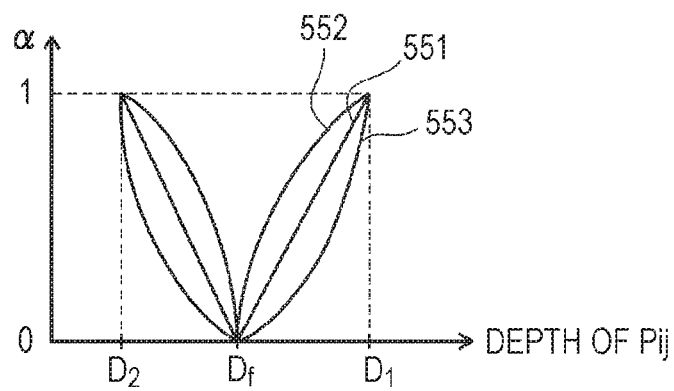

An outline is illustrated in FIGS. 14A to 14C. For the observation point Pij on a straight line 530 orthogonal to the transducer element array illustrated in FIG. 14A, calculation is performed as follows. First, for observation points R1, R3 existing on boundaries inside and outside the ultrasound main irradiation area, and the observation point in the ultrasound main irradiation area, the calculation method is used based on the transmission focal point F as a reference. That is, for the observation point R1, the transmission time $T_R$ is calculated on the basis of a total of a path 531 and a path 532, and for the observation point R2, the transmission time $T_R$ is calculated on the basis of a difference between the path 531 and the path 535. Similarly, the transmission time $T_R$ is calculated on the basis of a total of the path 531 and a path from the transmission focal point F to the observation point P, for an observation point P deeper than the observation point R1, and is calculated on the basis of the difference between the path 531 and a path from the observation point P to the transmission focal point F, for an observation point P shallower than the observation point R1.

For the observation point R2 having the same depth as the transmission focal point F, the transmission time $T_D$ is calculated on the basis of a path 536 from the center of the transmission aperture Tx to the observation point R2.

Further, for the observation point P existing between the observation point R1 and the observation point R2, weighted synthesis is performed to the transmission time $T_R$ based on the transmission focal point F, and the transmission time $T_D$ based on the path 535 from the center of the transmission aperture Tx to the observation point P. For example, the following equation can be used.

$$T_M = \alpha T_R + (1-\alpha) T_D$$

Here, the value of $\alpha$ preferably satisfies two conditions: $\alpha=0$ when $D=Df$, and $\alpha=1$ when $D=D1$ or $D2$, as illustrated in FIG. 14C. Incidentally, Df, D1, and D2 are the depths of the transmission focal point F, the observation point R1, and observation point R2, respectively. This is because the transmission time has a continuous and monotonic increasing relationship to the depth of the observation point Pij as illustrated in a straight line 543 of FIG. 14B, in this way. Incidentally, in FIG. 14B, a straight line 542 represents the transmission time $T_D$, and two discontinuous straight lines 541 represent the transmission time $T_R$. Incidentally, assuming that $\alpha$ is proportional to $|D-Df|$, for example, the value of $\alpha$ may be a value represented by the following equation, for example.

$$\alpha = (D-Df)/(D1-Df) (D1 > D \geq Df)$$

$$\alpha = (Df-D)/(Df-D2) (Df > D > D2)$$

That is, the relationship may be the one represented by a polygonal line 551 of FIG. 14C. Incidentally, a specific example of $\alpha$ is not limited to the above examples, and it is sufficient that the transmission time has a continuous and monotonic increasing relationship to the depth of the observation point Pij, and may be a value represented by a curve 552 or curve 553.

Incidentally, any one of the following equations may be used.

$$T_M = \alpha T_R + (1-\alpha) T_P$$

$$T_M = \alpha T_R + (1-\alpha) T_N$$

$$T_M = \alpha T_P + (1-\alpha) T_P$$

$$T_M = \alpha T_P + (1-\alpha) T_N$$

$$T_M = \alpha T_P + (1-\alpha) T_P$$

$$T_M = \alpha T_P + (1-\alpha) T_N$$

Alternatively, any one of the following relationships may be used.

$$T_M = T_R^\alpha \times T_D^{(1-\alpha)}$$

$$T_M = T_R^\alpha \times T_P^{(1-\alpha)}$$

$$T_M = T_R^\alpha \times T_N^{(1-\alpha)}$$

$$T_M = T_P^\alpha \times T_D^{(1-\alpha)}$$

$$T_M = T_P^\alpha \times T_N^{(1-\alpha)}$$

$$T_M = T_D^\alpha \times T_P^{(1-\alpha)}$$

$$T_M = T_D^\alpha \times T_N^{(1-\alpha)}$$

<Relationship Between Calculation Method and Target Area>

In the first embodiment, the transmission time $T_R$ is applied to the target areas Bx1A, Bx2A, Bx3A, and the transmission time $T_D$ is applied to the target areas Bx1B, Bx2B, Bx3B. However, the calculation method is not limited to this case, and it is sufficient that a suitable calculation method is applied for each area, and (1) different calculation methods may be applied respectively to the main target area Bx1A and the main target area Bx1B, and (2) a different calculation method may be applied to at least one of the sub-target areas Bx2A, Bx3A, Bx2B, and Bx3B.

For example, transmission time $T_R$ may be applied to the main target area Bx1A, Bx1B, the transmission time $T_D$ may be used in the sub-target areas Bx2A, Bx3A, and the transmission time $T_P$ may be used in the sub-target areas Bx2B, Bx3B. Alternatively, for example, the transmission time $T_M$ may be applied to the main target areas Bx1A, Bx1B, the transmission time $T_D$, may be used in the sub-target areas Bx2A, Bx3A, and the transmission time $T_D$ may be used in the sub-target areas Bx2B, Bx3B. Further, for example, the transmission time $T_c$ may be used in the sub-target areas Bx2B, Bx3B, and the transmission time $T_R$ may be used in all other areas.

Figure 15A:
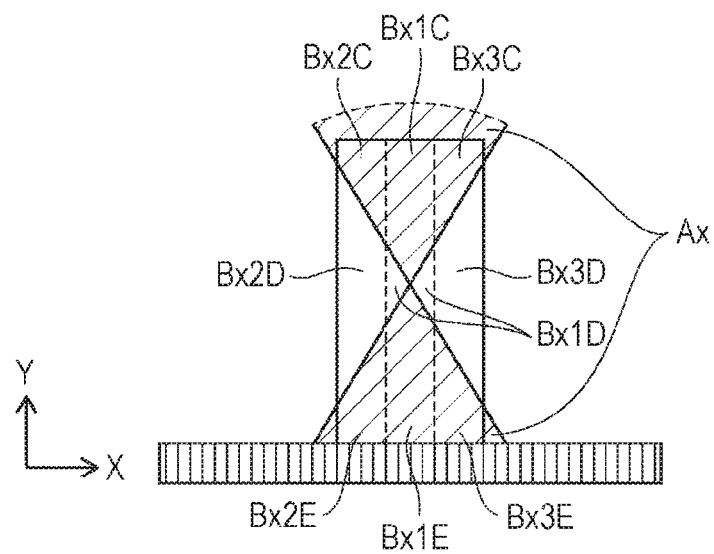
FIGS. 15A and 15B are both schematic views illustrating a target area of another embodiment.

The method for dividing the main target area and the sub-target area by the depth is not limited to the example of using the focal depth as a reference as illustrated in FIG. 5. For example, the area may be divided into the inside and outside of the ultrasound main irradiation area Ax instead of being divided by the transmission focal depth. For example, each of the main target area Bx1, and the sub-target areas Bx2, Bx3 can be divided depending on whether the area is the inside or outside of the ultrasound main irradiation area Ax as illustrated in FIG. 15A. That is, the main target area Bx1 may be divided into Bx1D that is outside the ultrasound main irradiation area Ax, Bx1C that is inside the ultrasound main irradiation area Ax and deeper than the focal depth, and Bx1E that is inside the ultrasound main irradiation area Ax and shallower than the focal depth, and similarly, the sub-target area Bx2 may be divided from the deeper side into Bx2C, Bx2D, Bx2E, and the sub-target area Bx3 may be divided from the deeper side into Bx3C, Bx3D, Bx3E. In this case, (1) a different calculation method may be applied to at least one of the main target areas Bx1C, Bx1D, Bx1E, and (2) a different calculation method may be applied to at least one of the sub-target areas Bx2C, Bx3C, Bx2D, Bx3D, Bx2E, Bx3E.

For example, the transmission time $T_R$ may be applied to the areas Bx1C, Bx2C, Bx3C, Bx1E, Bx2E, Bx3E, and the transmission time $T_M$ may be applied to the areas Bx1D, Bx2D, Bx3D. In addition, the transmission time $T_R$ may be applied to the areas Bx1C, Bx1E, the transmission time $T_M$ may be applied to the area Bx1D, and the transmission time $T_D$ may be applied to all other areas, for example.

Figure 15B:
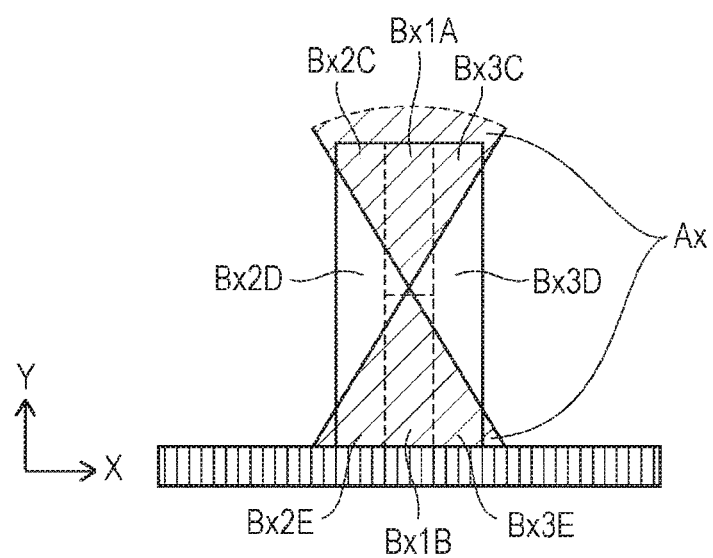

Further, the method may be changed for dividing the area in the depth direction between the main target area Bx1 and the sub-target areas Bx2, Bx3, as illustrated in FIG. 15B.

Incidentally, the relationship between the calculation method and the target area is not limited to the above examples, and as far as the reception beam forming suitable for the observation point Pij is applied, any method can be used for dividing the area, and any method can be used for applying the reception beam forming to each area.

Second Embodiment

In the first embodiment, for the multiple complex acoustic lines acquired from the same observation point, the velocity estimator 1053 does not distinguish the transmission event set from which the complex acoustic lines are acquired, and uses the complex acoustic lines all as ensembles. In a second embodiment, configurations of the transmission beam former and the reception beam former are similar to those in the first embodiment; however, processing of velocity estimation differs from that in the first embodiment. In the first embodiment, for the same observation point, there is no distinction among the complex acoustic line signal acquired inside the target area Bx1, the complex acoustic line signal acquired inside the sub-target area Bx2, and the complex acoustic line signal acquired inside the sub-target area Bx3. Among the main target area Bx1, the sub-target area Bx2, and the sub-target area Bx3, the reception beam forming method, specifically, the method for calculating the transmission time is not necessary to be the same as each other. In that case, when all are used as ensembles when the reception beam forming method differs between the complex acoustic line signal acquired inside the main target area Bx1 and the complex acoustic line signal acquired inside the sub-target area Bx2, there may be a case in which difference of the method for calculating the transmission time is detected as a phase difference of the complex acoustic line signals. Specifically, it is assumed that there are ten complex acoustic line signals acquired inside the main target area Bx1, and ten complex acoustic line signals acquired inside the sub-target area Bx2. As described above, the phase difference between two complex acoustic line signals corresponds to an average velocity from acquisition of one to acquisition of the other. However, in the phase difference between one of the complex acoustic line signals acquired inside the main target area Bx1 and one of the complex acoustic line signals acquired inside the sub-target area Bx2, influence may occur due to the difference in the reception beam forming method between the main target area Bx1 and the sub-target area Bx2. Such influence does not occur in the phase difference between two complex acoustic line signals acquired inside the main target area Bx1, and the phase difference between two complex acoustic line signals acquired inside the sub-target area Bx2. For that reason, when the multiple complex acoustic line signals obtained by different reception beam forming methods are treated as a series of ensembles, there may be a case in which accuracy of the average velocity is not sufficiently increased.

The ultrasound diagnostic device of the second embodiment differs from the first embodiment in that the device estimates the average velocity for each observation point within the target area Bx for each of the transmission event sets, and generates the color Doppler image by performing average velocity synthesis between the transmission event sets.

<Configuration>

Figure 16:
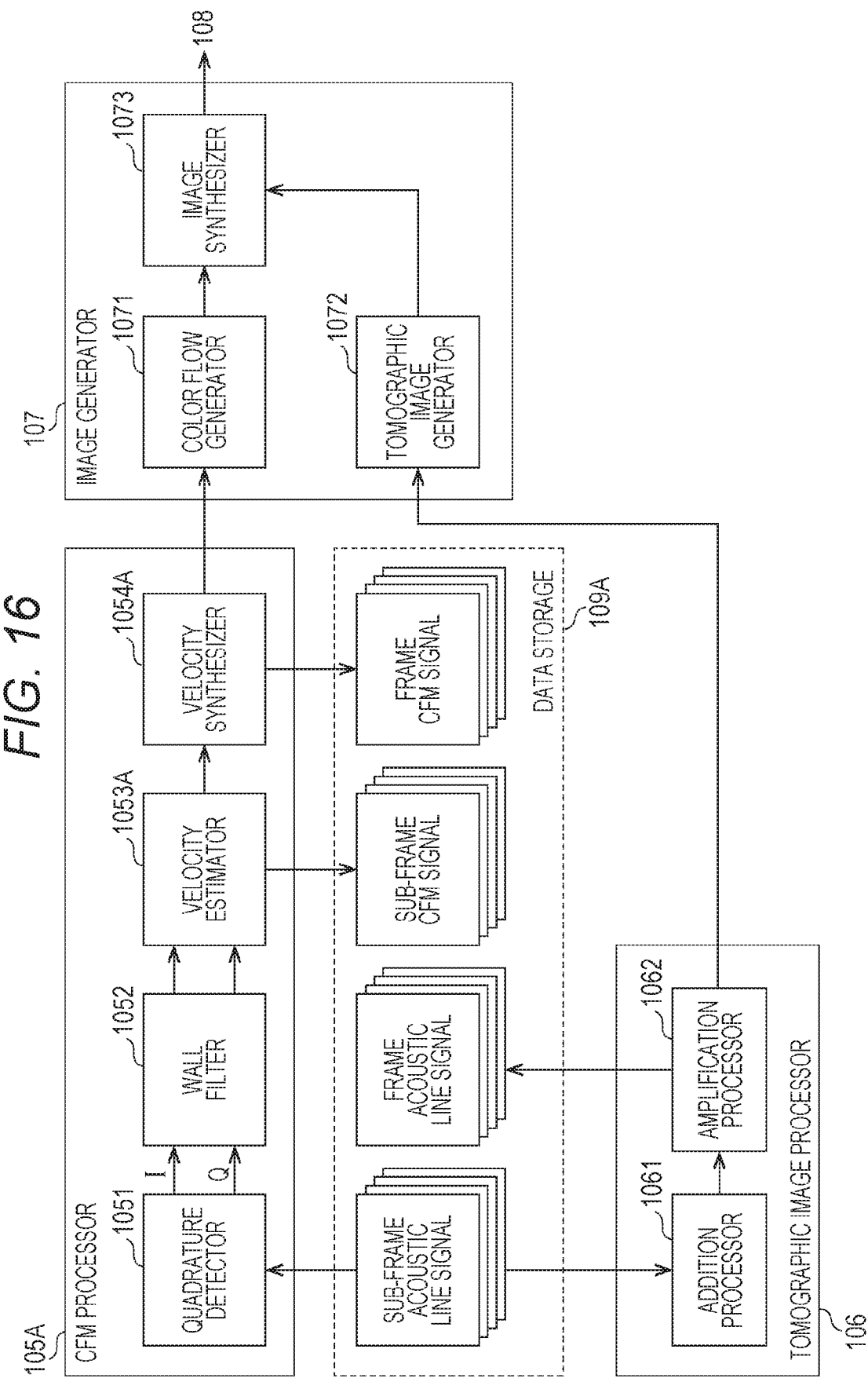
FIG. 16 is a functional block diagram illustrating configurations of a CFM processor, a tomographic image processor, and an image generator of a second embodiment.

Hereinafter, the ultrasound diagnostic device of the second embodiment will be described with reference to the drawings. FIG. 16 is a functional block diagram illustrating a configuration of a CFM processor 105A of the ultrasound diagnostic device of the second embodiment. The CFM processor 105A of the second embodiment includes: a velocity estimator 1053A for estimating the average velocity of each observation point, for each of the transmission event sets; and a velocity synthesizer 1054A for synthesizing the average velocities estimated between the transmission event sets. The configuration other than the velocity estimator 1053A and the velocity synthesizer 1054A is the same as that of each component described in the first embodiment, and the description will be omitted for the same part.

(1) Velocity Estimator 1053A

The velocity estimator 1053A is a circuit for estimating movement, specifically the bloodstream, within the subject corresponding to each observation point, from the complex acoustic line signal after being subjected to the filter processing, in synchronization with the transmission event set. The velocity estimator 1053A estimates the phase from each complex acoustic line signal corresponding to each of the multiple transmission events of each transmission event sets, and calculates a change rate of the phase, for each observation point. That is, even when the complex acoustic line signals are related to the same observation point, the complex acoustic line signals of the different transmission event sets are not used at the same time. For example, for the observation point P within the sub-target area Bx3A in a certain transmission event set, ten complex acoustic line signals are obtained for each of the transmission event sets, for the observation point within the main target area Bx1A in the next transmission event set, and for the observation point within the sub-target area Bx2A in the further next transmission event set. At this time, for the observation point P, the average velocity is estimated from each of ten complex acoustic line signals of the first transmission event set, ten complex acoustic line signals of the second transmission event set, and ten complex acoustic line signals of the third transmission event set. That is, three average velocities are estimated for the same observation point. The velocity estimator 1053A generates a sub-frame CFM signal in which the average velocities are made to be a signal sequence continuing in the transmission direction (depth direction of the subject) of the ultrasound, and outputs the signal to the data storage 109.

(2) Velocity Synthesizer 1054A

The velocity synthesizer 1054A is a circuit for synthesizing multiple sub-frame CFM signals to generate a frame CFM signal. The velocity synthesizer 1054A reads a series of sub-frame CFM signals configuring one frame. Then, the average velocity is synthesized using as an index the position of observation point Pij included in each sub-frame CFM signal.

Figure 17:
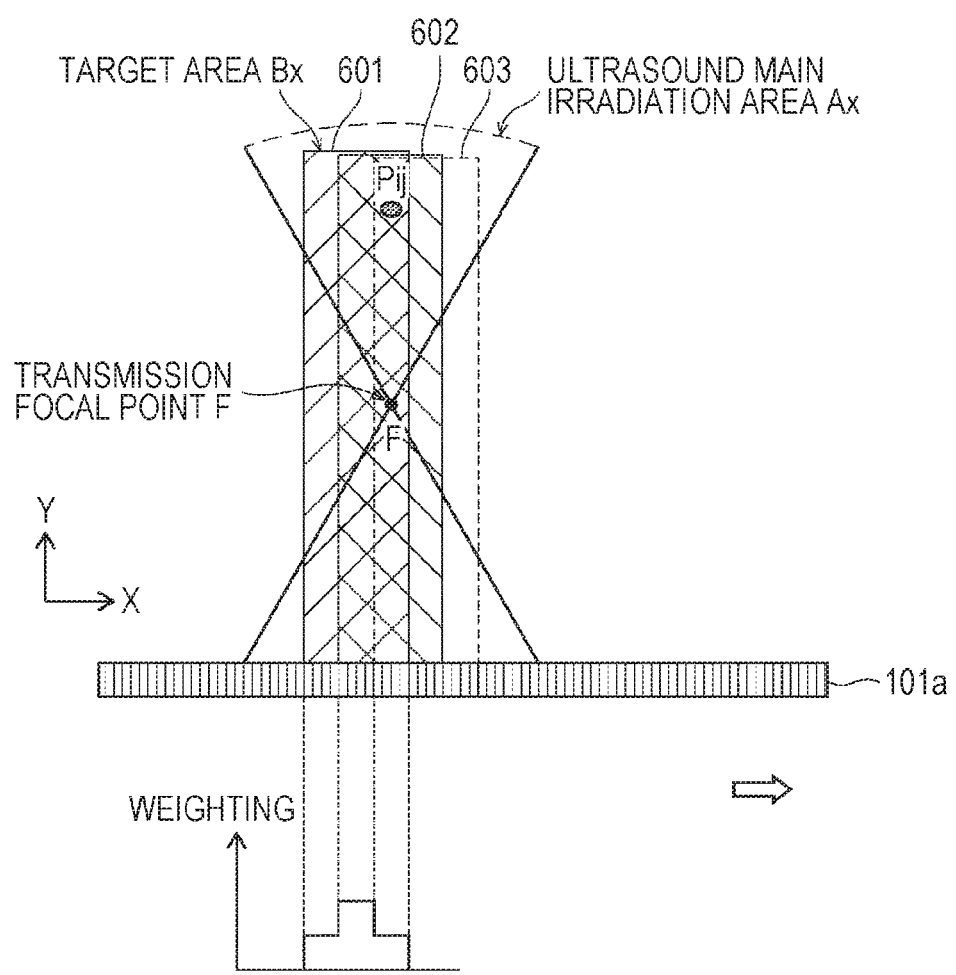
FIG. 17 is a schematic view illustrating processing for synthesizing an average velocity in a velocity synthesizer of the second embodiment.

FIG. 17 is a schematic view illustrating processing for synthesizing the average velocity in the velocity synthesizer 1054A. As described above, ultrasound transmission is sequentially performed while the transducer element to be used for the transmission aperture Tx is made to differ by the shift pitch in the transducer element array direction in synchronization with the transmission event set. For that reason, the average velocity of the observation point Pij is estimated for each of the transmission event set having an area 601 as the target area Bx, the transmission event set having an area 602 as the target area Bx, and the transmission event set having an area 603 as the target area Bx. One frame CFM signal is synthesized by synthesizing the multiple average velocities using the position of the observation point Pij as an index.

As a method for synthesizing the multiple average velocities, an arithmetic average can be used such as a simple arithmetic mean or geometric mean. In addition, for example, weighting may be performed using as an index whether the observation point belongs to the main target area Bx1 or the sub-target areas Bx2, Bx3 in the transmission event set, as illustrated in FIG. 17. For example, for the observation point Pij, weighting is made larger for the transmission event set having the area 602 as the target area Bx in which Pij is included in the main target area Bx1 than for the transmission event set having the area 601 or area 603 as the target area Bx in which Pij is included in the sub-target area Bx2 or Bx3. More specifically, for the observation point Pij, a weighting factor is set to ½ for the average velocity of the transmission event set having the area 602 as the target area Bx, and a weighting factor is set to ¼ for each average velocity in the transmission event set having the area 601 and the area 603 as the target area Bx, and a result of addition processing is set as the average velocity of the observation point Pij. In this way, the weighting factor of the average velocity estimated from the observation point inside the main target area Bx1 is made larger than the weighting factor of the average velocity estimated from the observation point inside the sub-target areas Bx2, Bx3, whereby the average velocity can be made close to that based on the acoustic line signal acquired in the transmission event set of when the transmission focal point F is close, and accuracy of the average velocity can be improved, for each observation point. Incidentally, the weighting factor is not limited to the above example, and it is sufficient that the weighting factor of the average velocity estimated from the observation point inside the main target area is equal to or greater than the weighting factor of the average velocity estimated from the observation point inside the sub-target area.

The velocity synthesizer 1054A generates the frame CFM signal in which the calculated average velocities after synthesis are made to be a signal sequence continuing in the transmission direction (depth direction of the subject) of the ultrasound, and outputs the signal to the data storage 109.

<Operation>

Figure 18:
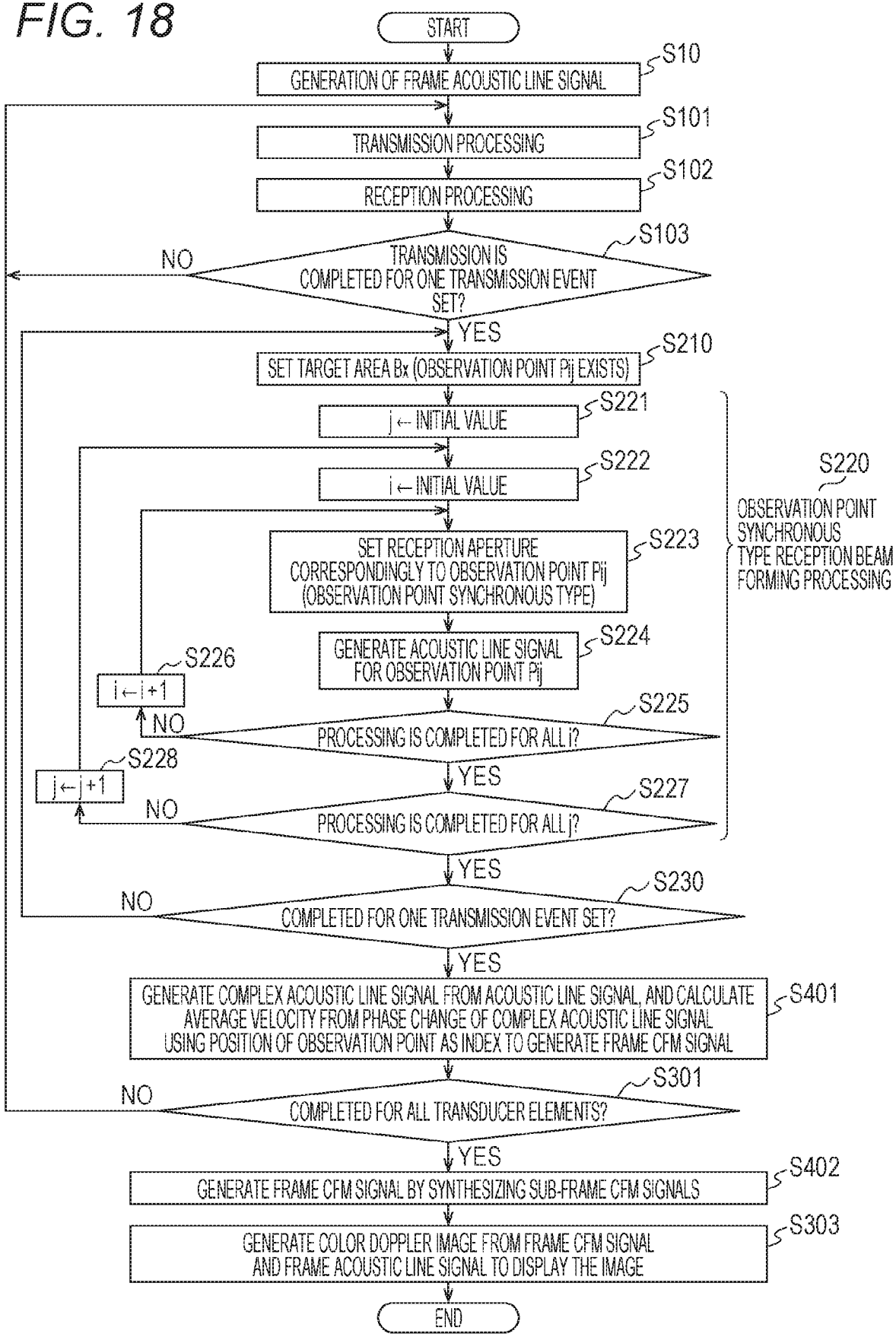
FIG. 18 is a flowchart illustrating operation of an ultrasound diagnostic device of the second embodiment.

FIG. 18 is a flowchart illustrating operation of the ultrasound diagnostic device of the second embodiment. The flowchart differs from that of FIG. 10 in that step S402 is performed instead of average velocity calculation processing (S302) in FIG. 10, and step S401 is further performed between step S230 and step S301. The processing other than the above is the same as that of FIG. 10, and the description will be omitted for the same part.

In the processing of step S401, the velocity estimator 1053A of the CFM processor 105A reads the multiple acoustic line signals stored in the data storage 109 in synchronization with the transmission event set, and calculates the average velocity from the phase change of the complex acoustic line signal, using the position of the observation point Pij as an index. First, the quadrature detector 1051 performs quadrature detection to each acoustic line signal read to convert the signal to the complex acoustic line signal, and the filter 1052 excludes or reduces the clutter from the complex acoustic line signal. Next, the velocity estimator 1053A estimates the change rate of the phase by performing correlation processing to the multiple complex acoustic line signals acquired in one transmission event set of the same observation point Pij. Further, the velocity estimator 1053A calculates the Doppler shift amount from the change rate of the phase estimated, calculates the velocity from the Doppler shift amount, and calculates the average value of the velocity. Finally, the velocity estimator 1053A generates the sub-frame CFM signal by associating the average velocity calculated with the observation point, and outputs the signal to the data storage 109. After that, it is determined whether or not ultrasound transmission is completed from all transducer elements 101$a$ existing in the probe 101 (step 230), and when the transmission is not completed, the operation returns to step S101, and the transmission event set is performed after the ultrasound transmission aperture Tx is shifted by a shift step Mp in the array direction. When the ultrasound transmission is completed, the operation proceeds to step S401. Thus, the sub-frame CFM signal generated for each of the transmission event sets has been stored in the data storage 109.

Next, the sub-frame CFM signal is synthesized and the frame CFM signal is generated (step S402). The velocity synthesizer 1054A reads the series of sub-frame CFM signals configuring one frame. Then, the average velocity is synthesized using as an index the position of observation point Pij included in each sub-frame CFM signal. The velocity synthesizer 1054A generates the frame CFM signal in which the calculated average velocities after synthesis are made to be a signal sequence continuing in the transmission direction (depth direction of the subject) of the ultrasound, and outputs the signal to the data storage 109.

After that, the color Doppler image is generated from the frame CFM signal and the frame acoustic line signal, and is displayed (step S303), and then processing is ended.

<Effect>

As described above, with the ultrasound diagnostic device of the second embodiment, it is possible to reduce the number of times of transmission and reception of ultrasound while keeping the ensemble number, and to improve the frame rate while keeping quality of the color Doppler image, similarly to the ultrasound diagnostic device 100 of the first embodiment.

Further, in the ultrasound diagnostic device of the second embodiment, synthesis is performed between the transmission event sets, after estimating the average velocity in synchronization with the transmission event set. For that reason, there is no possibility that the difference in the reception beam forming method in each area within the target area influences the average velocity, and it is possible to further improve accuracy of the average velocity while performing optimal reception beam forming for each area.

Other Modifications of Embodiments (1) In each embodiment and each modification, the phasing adder 1041 performs observation point synchronous type reception beam focusing processing when performing phasing addition for the observation point Pij; however, the present invention is not necessarily limited to this case. For example, transmission aperture synchronous type reception beam focusing processing may be performed. In the transmission aperture synchronous type reception beam focusing processing, the reception aperture Rx is controlled so that the array center of the reception aperture Rx and the array center of the transmission aperture Tx coincide with each other, and the weight sequence is calculated so that weight is the maximum for the transducer element positioned at the array center of the transmission aperture Tx. In this way, a different reception aperture Rx can be used for each of the transmission event sets, for one observation point Pij, and spatial resolution can be made uniform.

(2) In each embodiment and each modification, the width in the array direction of each of the main target area Bx1 and two sub-target areas Bx2, Bx3 coincides with the shift pitch; however, the present invention is not necessarily limited to this case. For example, the width in the array direction of each of the main target area Bx1 and two sub-target areas Bx2, Bx3 may be greater than the shift pitch.

In addition, the widths in the array direction of the main target area Bx1 and two sub-target areas Bx2, Bx3 are not necessarily the same as each other. For example, the width of the main target area Bx1 may be the width of six elements, and the width of each of the sub-target areas Bx2, Bx3 may be the width of four elements.

Further, it is not necessary that both of two areas Bx2, Bx3 are the sub-target areas, and only Bx2, or only Bx3 may be used as the sub-target area.

(3) In each embodiment and each modification, the color flow generator 1071 generates the color Doppler image by converting the average velocity of each observation point into color information; however, the present invention is not necessarily limited to this case. For example, the velocity estimator 1053 may generate a frame power signal by calculating power from a power spectrum of each observation point, and the color flow generator 1071 may convert the power value into a yellow luminance value, whereby a power Doppler image may be generated.

(4) In each embodiment and each modification, transmission and reception of ultrasound for acquiring the B mode tomographic image is performed separately from the color flow mapping method; however, the tomographic image processor 106 may generate the frame acoustic line signal by using the acoustic line signal acquired for the color flow mapping method, for example. At this time, the tomographic image processor 106 is capable of repeating operation for selecting one of the multiple sub-frame acoustic line signals acquired in each of the multiple transmission events of one transmission event set, for the multiple events of one frame, and synthesizing the multiple sub-frame acoustic line signals selected using the position of the observation point Pij as an index, to generate the frame acoustic line signal.

(5) Incidentally, the present invention has been described on the basis of the above embodiments; however, the present invention is not limited to the above embodiments, and the following cases are also included in the present invention.

For example, the present invention may be a computer system including a microprocessor and a memory, and the memory may store a computer program, and the microprocessor may operate in accordance with the computer program. For example, the present invention may be a computer system that has a computer program of a diagnostic method of the ultrasound diagnostic device of the present invention and operates in accordance with the program (or instructs operation to each component connected).

The present invention also includes a case in which all or some of the ultrasound diagnostic device, and all or some of the beam former are configured by a computer system configured by a microprocessor, recording media such as ROM and RAM, a hard disk unit, and the like. The RAM or the hard disk unit stores a computer program for achieving similar operation to that of each of the above devices. The microprocessor operates in accordance with the computer program, whereby each of the devices achieves its function.

Some or all of components configuring the above devices may be configured by one system large scale integration (LSI) (large scale integrated circuit). The system LSI is an extremely versatile LSI manufactured by integrating multiple components on one chip, and specifically is a computer system configured by including the microprocessor, ROM, and RAM. These components may be individually made into one chip, and may be made into one chip to include some or all of the components. Incidentally, the LSI is also referred to as an IC, system, LSI, super LSI, or ultra LSI, depending on the degree of integration. The RAM stores the computer program for achieving similar operation to that of each of the above devices. The microprocessor operates in accordance with the computer program, whereby the system LSI achieves its function. For example, the present invention also includes a case in which the beam forming method of the present invention is stored as a program of the LSI, and the LSI is inserted in a computer, and a predetermined program (beam forming method) is executed.

Incidentally, the method for circuit integration is not limited to the LSI, and may be implemented by a dedicated circuit or a general-purpose processor. A field programmable gate array (FPGA) that can be programmed after LSI manufacture, or a reconfigurable processor in which connections and settings of circuit cells in the LSI can be reconfigured may be used.

Further, when an integrated circuit technology appears that replaces the LSI due to progress of the semiconductor technology or another derivative technology, naturally, integration of functional blocks may be performed by using the integrated circuit technology.

In addition, some or all of functions of the ultrasound diagnostic device of each embodiment may be implemented by causing the processor such as the CPU to execute the program. The present disclosure may be a non-transitory computer readable recording medium in which the program is recorded for executing the diagnostic method of the ultrasound diagnostic device and beam forming method. The program may be executed by another independent computer system by recording and transferring the program and the signal in the recording medium, and the program can be distributed via a transmission medium such as the Internet, of course.

Each component of the ultrasound diagnostic device of the above embodiments may have a configuration implemented by a programmable device such as a central processor (CPU), graphics processor (GPU), or processor, and software. The latter configuration is a so-called general-purpose computing on graphics processor (GPGPU). These components can be one circuit part, and can be an assembly of multiple circuit parts. In addition, multiple components can be combined to make one circuit part, and can be an assembly of multiple circuit parts.

The ultrasound diagnostic device of the above embodiments is configured to include the data storage that is a storage device, in the ultrasound diagnostic device; however, the storage device is not limited thereto, and the ultrasound diagnostic device may have a configuration in which a semiconductor memory, hard disk drive, optical disk drive, magnetic storage device, and the like are externally connected to the ultrasound diagnostic device.

In addition, the division of functional blocks in the block diagram is an example, and multiple functional blocks may be implemented as one functional block, one functional block may be divided into multiple blocks, and some functions may be transferred to other functional blocks. In addition, functions of multiple functional blocks having similar functions may be processed by a single piece of hardware or software in parallel or on a time-sharing basis.

The order in which the above steps are executed is exemplified for specifically describing the present invention, and may be in order other than the above. In addition, some of the above steps may be executed simultaneously (in parallel) with other steps.

In addition, the probe and the display are externally connected to the ultrasound diagnostic device; however, the probe and the display may be included in the ultrasound diagnostic device integrally.

As for the probe, a probe configuration is described in which multiple piezoelectric elements are arranged in a one-dimensional direction, in the above embodiments. However, the probe configuration is not limited thereto, and for example, a two-dimensional array transducer element in which multiple piezoelectric conversion elements are arranged in a two-dimensional direction, or an oscillating probe for acquiring a three-dimensional tomographic image by mechanically oscillating multiple transducer elements arranged in a one-dimensional direction may be used, and those can be selectively used depending on the measurement if appropriate. For example, when the two-dimensionally arranged probe is used, it is possible to control an irradiation position and direction of the ultrasound beam to be transmitted by individually changing the timing of applying voltage to the piezoelectric conversion element and the value of the voltage.

The probe may be configured to include some functions of a transmitter and receiver. For example, on the basis of a control signal for generating a transmission electric signal output from the transmitter and receiver, the transmission electric signal is generated in the probe, and the transmission electric signal is converted into ultrasound. In addition, reflected ultrasound received is converted into a reception electric signal, and a received signal is generated on the basis of the reception electric signal, in the probe.

At least some of the functions may be combined of the ultrasound diagnostic device of each embodiment and its modification. In addition, the numbers used in the above are all exemplified for specifically describing the present invention, and the present invention is not limited to the numbers exemplified.

Further, various modifications to which changes are made to the present embodiments in a range that can be conceived by those skilled in the art are also included in the present invention.

<<Summary>>

(1) An ultrasound signal processor of an embodiment is an ultrasound signal processor that selectively drives a plurality of transducer elements arrayed in an ultrasound probe and executes ultrasound transmission and reception to a subject to perform velocity analysis by a color flow mapping method, the ultrasound signal processor including: a transmitter configured to select a transmission transducer element array from the plurality of transducer elements, and perform transmission from the transmission transducer element array such that ultrasound focuses within the subject, for a plurality of transmission events included in one of transmission event sets; a receiver configured to generate a received signal sequence for a transducer element of a reception transducer element array selected from the plurality of transducer elements, based on reflected ultrasound received by the transducer element, for each of the transmission events; a phasing adder configured to generate an acoustic line signal, for each of the transmission events, for a plurality of observation points included in a main target area including an area corresponding to an area in which the ultrasound focuses within the subject and a sub-target area adjacent to the main target area in an array direction, by performing phasing addition to the received signal sequence based on the reflected ultrasound obtained from each of the observation points; and a velocity calculator configured to generate a complex acoustic line signal by performing quadrature detection to the acoustic line signal for each of the transmission events, and calculate an average velocity, based on time change of a phase of the complex acoustic line signal for each of the observation points, wherein the phasing adder performs delay processing for changing a method for calculating a transmission time in which the ultrasound transmitted reaches each of the observation points, depending on a depth of each of the observation points, in at least one of the main target area and the sub-target area.

An ultrasound signal processing method of an embodiment is an ultrasound signal processing method that selectively drives a plurality of transducer elements arrayed in an ultrasound probe and executes ultrasound transmission and reception to a subject to perform velocity analysis by a color flow mapping method, the ultrasound signal processing method including: selecting a transmission transducer element array from the plurality of transducer elements, and transmitting ultrasound from the transmission transducer element array such that the ultrasound focuses within the subject, for a plurality of transmission events included in one of transmission event sets; generating a received signal sequence for a transducer element of a reception transducer element array selected from the plurality of transducer elements, based on reflected ultrasound received by the transducer element, for each of the transmission events; generating an acoustic line signal, for each of the transmission events, for a plurality of observation points included in a main target area including an area corresponding to an area in which the ultrasound focuses within the subject and a sub-target area adjacent to the main target area in an array direction, by performing phasing addition to the received signal sequence based on the reflected ultrasound obtained from each of the observation points, by performing delay processing for changing a method for calculating a transmission time in which the ultrasound transmitted reaches each of the observation points depending on a depth of each of the observation points, in at least one of the main target area and the sub-target area; and generating a complex acoustic line signal by performing quadrature detection to the acoustic line signal for each of the transmission events, and, for each of the observation points, calculating an average velocity, based on time change of a phase of the complex acoustic line signal.

With an ultrasound signal processor, an ultrasound signal processing method, and an ultrasound diagnostic device using the processor and the method of one aspect of the present invention, quality of an acoustic line signal can be improved by switching reception beam forming for observation points included in a main target area and a sub-target area, and thus the frame rate can be improved by a technique for reducing the number of transmission event sets. Therefore, an increase in the number of times of transmission event due to an increase in the ensemble number can be canceled by reducing the number of transmission event sets, and quality of the color Doppler image can be improved by increasing the ensemble number while keeping the frame rate.

(2) The ultrasound signal processor of the above (1) is preferably configured such that the transmitter selects the transmission transducer element array from the plurality of transducer elements for each of the transmission events such that the transducer element array for transmitting the ultrasound shifts by a pitch of the plurality of transducer elements in the array direction, in synchronization with the transmission event set, and widths in the array direction of the main target area and the sub-target area are each at least equal to or greater than the pitch.

With the above configuration, for the same observation point, the acoustic line signal can be acquired in two or more transmission event sets, and the ensemble number can be surely increased.

(3) The ultrasound signal processor of the above (1) is preferably configured such that the transmitter selects the transmission transducer element array from the plurality of transducer elements for each of the transmission events such that the transducer element array for transmitting the ultrasound shifts by the pitch of the plurality of transducer elements in the array direction, in synchronization with the transmission event set, the sub-target area includes a first sub-target area and a second sub-target area, and the first sub-target area, the main target area, and the second sub-target area are lined up in this order in the array direction in each of the transmission event sets, and widths of the main target area, the first sub-target area, and the second sub-target area in the array direction are each at least equal to or greater than the pitch.

With the above configuration, for the same observation point, the acoustic line signal can be acquired in three or more transmission event sets, and the ensemble number can be surely increased.

(4) The ultrasound signal processor of the above (1)-(3) is preferably configured such that the method for calculating the transmission time differs between a case in which a depth of each of the observation points is equal to or greater than a focal depth at which the ultrasound focuses within the subject and a case in which the depth of each of the observation points is less than the focal depth, in the phasing adder.

With the above configuration, it is possible to perform switching of the reception beam forming depending on the depth of the observation point on the basis of the transmission focal point as a reference, and improve quality of the acoustic line signal to improve accuracy of the average velocity.

(5) The ultrasound signal processor of the above (1)-(3) is preferably configured such that the method for calculating the transmission time differs between a case in which each of the observation points is included in an area where the transmission transducer element array is a base, a width in the array direction is smallest corresponding to the focal depth at which the ultrasound focuses within the subject, and the width in the array direction increases corresponding to a depth having a great difference from the focal depth, and a case in which each of the observation points is not included in the area, in the phasing adder.

With the above configuration, it is possible to perform switching of the reception beam forming according to the beam forming of transmission ultrasound, and improve quality of the acoustic line signal to improve accuracy of the average velocity.

(6) The ultrasound signal processor of the above (1)-(5) is preferably configured such that the method for calculating the transmission time differs between a first observation point within the main target area and a second observation point that exists within the sub-target area and has the same depth as the first observation point, in the phasing adder.

With the above configuration, it is possible to perform switching of the reception beam forming according to the position in the array direction of the observation point, and improve quality of the acoustic line signal to improve accuracy of the average velocity.

(7) The ultrasound signal processor of the above (1)-(6) is preferably configured such that the velocity calculator, for each of the transmission event sets, calculates an average velocity as a first velocity for an observation point included within the main target area, and calculates an average velocity as a second velocity for an observation point included within the sub-target area, and further, for an observation point corresponding to the same position within the subject, calculates an average velocity of the observation point from the first velocity of the observation point and the second velocity of the observation point.

With the above configuration, accuracy of the average velocity can be kept high even when the reception beam forming differs between the transmission event sets, for the observation point.

(8) The ultrasound signal processor of the above (1)-(6) is preferably configured such that the velocity calculator, from an average of a time change amount of the phase of the complex acoustic line signal in an observation point corresponding to the same position within the subject acquired in the plurality of transmission event sets, calculates an average velocity of the observation point.

With the above configuration, regardless of the transmission event set, it is possible to use all acoustic line signals related to the observation point as ensembles, and improve accuracy of the average velocity by increasing the ensemble number.

(9) The ultrasound signal processor of the above (1)-(8) is preferably configured such that the phasing adder calculates as the transmission time a total of a first time and a second time when the depth of each of the observation points is equal to or greater than the focal depth at which the ultrasound focuses within the subject, wherein the first time is a time in which the ultrasound transmitted reaches a reference point in an area at which the ultrasound focuses from the transmission transducer element array, and the second time is a time in which the ultrasound transmitted reaches each of the observation points from the reference point, and the phasing adder calculates as the transmission time a result of subtracting the second time from the first time when the depth of each of the observation points is less than the focal depth at which the ultrasound focuses within the subject, as one method for calculating the transmission time.

With the above configuration, it is possible to improve quality of the acoustic line signal, and improve accuracy of the average velocity, for the area in which it is appropriate to calculate the transmission time on the basis of the transmission focal point as a reference.

(10) The ultrasound signal processor of the above (1)-(9) is preferably configured such that the phasing adder calculates as the transmission time a time in which the ultrasound transmitted reaches each of the observation points from an array center of the transmission transducer element array, as one method for calculating the transmission time.

With the above configuration, it is possible to improve quality of the acoustic line signal, and improve accuracy of the average velocity, for an area in which it is appropriate to calculate the transmission time on the basis of the shortest distance between the observation point and the array center of the transmission transducer element array.

(11) The ultrasound signal processor of the above (1)-(10) is preferably configured such that the phasing adder calculates as the transmission time a shortest time in which the ultrasound transmitted reaches each of the observation points from the transmission transducer element array, as one method for calculating the transmission time.

With the above configuration, it is possible to improve quality of the acoustic line signal, and improve accuracy of the average velocity, for an area in which it is appropriate to calculate the transmission time on the basis of the shortest distance between the observation point and the transmission transducer element array.

(12) The ultrasound signal processor of the above (1)-(11) is preferably configured such that the phasing adder calculates as the transmission time a value calculated by using two or more of (1) the total of the first time and the second time when the depth of each of the observation points is equal to or greater than the focal depth at which the ultrasound focuses within the subject, wherein the first time is the time in which the ultrasound transmitted reaches the reference point in the area at which the ultrasound focuses from the transmission transducer element array, and the second time is the time in which the ultrasound transmitted reaches each of the observation points from the reference point, and the result of subtracting the second time from the first time when the depth of each of the observation points is less than the focal depth at which the ultrasound focuses within the subject, (2) the time in which the ultrasound transmitted reaches each of the observation points from the array center of the transmission transducer element array, and (3) the shortest time in which the ultrasound transmitted reaches each of the observation points from the transmission transducer element array, as one method for calculating the transmission time.

With the above configuration, it is possible to improve quality of the acoustic line signal, and improve accuracy of the average velocity, for an area in which it is appropriate to calculate the transmission time on the basis of the shortest distance between the observation point and the transmission transducer element array.

(13) An ultrasound diagnostic device of an embodiment preferably includes the ultrasound signal processor of the above (1)-(11).

In this way, the ultrasound diagnostic device can be implemented including the above characteristics.

The ultrasound signal processor according to the present disclosure, the ultrasound signal processing method, and the ultrasound diagnostic device are useful as a color Doppler image generator that improves performance of a conventional ultrasound diagnostic device, and in particular achieves both ensemble number increase and frame rate improvement, and further improves accuracy of the average velocity.

Although the present invention has been described and illustrated in detail, it is clearly understood that the same is by way of illustrated and example only and is not to be taken byway of limitation, the scope of the present invention being interpreted by terms of the appended claims.

What is claimed is:

1. An ultrasound signal processor that selectively drives a plurality of transducer elements arrayed in an ultrasound probe and executes ultrasound transmission and reception to a subject to perform velocity analysis by a color flow mapping method, the ultrasound signal processor comprising:
   a transmitter configured to select a transmission transducer element array from the plurality of transducer elements, and perform transmission of ultrasound from the transmission transducer element array that is focussed within the subject, for a plurality of transmission events included in one of transmission event sets;
   a receiver configured to generate a received signal sequence for a transducer element of a reception transducer element array selected from the plurality of transducer elements, based on reflected ultrasound received by the transducer element of the reception transducer element array, for each of the transmission events;
   a phasing adder configured to generate an acoustic line signal, for each of the transmission events, for a plurality of observation points included in a main target area including an area corresponding to an area in which the ultrasound focuses within the subject and a sub-target area adjacent to the main target area in an array direction, by performing phasing addition to the received signal sequence based on the reflected ultrasound obtained from each of the observation points; and
   a velocity calculator configured to generate a complex acoustic line signal by performing quadrature detection to the acoustic line signal for each of the transmission events, and calculate an average velocity, based on time change of a phase of the complex acoustic line signal for each of the observation points, wherein
   the phasing adder performs delay processing for changing a method for calculating a transmission time in which the ultrasound transmitted reaches each of the observation points, depending on, in at least one of the main target area and the sub-target area, whether a depth of each of the observation points is equal to or greater than a focal depth at which the ultrasound focuses within the subject, and
   as one method of calculating the transmission time, the phasing adder adds a first time and a second time when the depth of each of the observation points is equal to or greater than the focal depth at which the ultrasound focuses within the subject, wherein the first time is a time in which the ultrasound transmitted reaches a reference point in an area at which the ultrasound focuses from the transmission transducer element array, and the second time is a time in which the ultrasound transmitted reaches each of the observation points from the reference point, and subtracts the second time from the first time when the depth of each of the observation points is less than the focal depth at which the ultrasound focuses within the subject.

2. The ultrasound signal processor according to claim 1, wherein
   the transmitter selects the transmission transducer element array from the plurality of transducer elements for each of the transmission events such that the transducer element array for transmitting the ultrasound shifts by a pitch of the plurality of transducer elements in the array direction, in synchronization with the transmission event set, and
   widths in the array direction of the main target area and the sub-target area are each at least equal to or greater than the pitch.

3. The ultrasound signal processor according to claim 1, wherein
the transmitter selects the transmission transducer element array from the plurality of transducer elements for each of the transmission events to shift the transducer element array for transmitting the ultrasound by the pitch of the plurality of transducer elements in the array direction, in synchronization with the transmission event set,
the sub-target area includes a first sub-target area and a second sub-target area, and the first sub-target area, the main target area, and the second sub-target area are lined up in this order in the array direction in each of the transmission event sets, and
widths of the main target area, the first sub-target area, and the second sub-target area in the array direction are each at least equal to or greater than the pitch.

4. The ultrasound signal processor according to claim 1, wherein
the method for calculating the transmission time differs between a case in which each of the observation points is included in an area where the transmission transducer element array is a base, a width in the array direction is smallest corresponding to the focal depth at which the ultrasound focuses within the subject, and the width in the array direction increases corresponding to an increase in a difference in depth from the focal depth, and a case in which each of the observation points is not included in the area where the transmission transducer element array is a base, in the phasing adder.

5. The ultrasound signal processor according to claim 1, wherein
the method for calculating the transmission time differs between a first observation point within the main target area and a second observation point that exists within the sub-target area and has the same depth as the first observation point, in the phasing adder.

6. The ultrasound signal processor according to claim 1, wherein
the velocity calculator, for each of the transmission event sets, calculates an average velocity as a first velocity for an observation point included within the main target area, and calculates an average velocity as a second velocity for an observation point included within the sub-target area, and further, for an observation point corresponding to the same position within the subject, calculates an average velocity of the observation point from the first velocity of the observation point and the second velocity of the observation point.

7. The ultrasound signal processor according to claim 1, wherein
the velocity calculator, from an average of a time change amount of the phase of the complex acoustic line signal in an observation point corresponding to the same position within the subject acquired in the plurality of transmission event sets, calculates an average velocity of the observation point.

8. The ultrasound signal processor according to claim 1, wherein
the phasing adder calculates as the transmission time a time in which the ultrasound transmitted reaches each of the observation points from an array center of the transmission transducer element array, as another method for calculating the transmission time.

9. The ultrasound signal processor according to claim 1, wherein
the phasing adder calculates as the transmission time a shortest time in which the ultrasound transmitted reaches each of the observation points from the transmission transducer element array, as another method for calculating the transmission time.

10. The ultrasound signal processor according to claim 1, wherein
the phasing adder calculates as the transmission time a value calculated by using two or more of (1) the time in which the ultrasound transmitted reaches each of the observation points from the array center of the transmission transducer element array, and (2) the shortest time in which the ultrasound transmitted reaches each of the observation points from the transmission transducer element array, as another method for calculating the transmission time.

11. An ultrasound diagnostic device comprising
the ultrasound signal processor according to claim 1 configured to be capable of connecting to the ultrasound probe.

12. An ultrasound signal processing method that selectively drives a plurality of transducer elements arrayed in an ultrasound probe and executes ultrasound transmission and reception to a subject to perform velocity analysis by a color flow mapping method, the ultrasound signal processing method comprising:
selecting a transmission transducer element array from the plurality of transducer elements, and transmitting ultrasound from the transmission transducer element array such that the ultrasound focuses within the subject, for a plurality of transmission events included in one of transmission event sets;
generating a received signal sequence for a transducer element of a reception transducer element array selected from the plurality of transducer elements, based on reflected ultrasound received by the transducer element, for each of the transmission events;
generating an acoustic line signal, for each of the transmission events, for a plurality of observation points included in a main target area including an area corresponding to an area in which the ultrasound focuses within the subject and a sub-target area adjacent to the main target area in an array direction, by performing phasing addition to the received signal sequence based on the reflected ultrasound obtained from each of the observation points, by performing delay processing for changing a method for calculating a transmission time in which the ultrasound transmitted reaches each of the observation points depending on, in at least one of the main target area and the sub-target area, whether a depth of each of the observation points is equal to or greater than a focal depth at which the ultrasound focuses within the subject,
wherein one method of calculating the transmission time includes adding a first time and a second time when the depth of each of the observation points is equal to or greater than the focal depth at which the ultrasound focuses within the subject, wherein the first time is a time in which the ultrasound transmitted reaches a reference point in an area at which the ultrasound focuses from the transmission transducer element array, and the second time is a time in which the ultrasound transmitted reaches each of the observation points from the reference point, and subtracting the second time from the first time when the depth of each of the observation points is less than the focal depth at which the ultrasound focuses within the subject; and generating a complex acoustic line signal by performing quadrature detection to the acoustic line signal for each of the transmission events, and, for each of the observation points, calculating an average velocity, based on time change of a phase of the complex acoustic line signal.

13. The ultrasound signal processor according to claim 1, wherein another method for calculating the transmission time when each of the observation points is at a depth less than a depth at which the ultrasound is focused includes determining that a transmission wave generated at the transmission aperture reaches the observation point at the same time that the transmission wave reaches a reference point having a same depth as the observation point.

* * * * *